(12) United States Patent
Tanner et al.

(10) Patent No.: US 10,737,005 B2
(45) Date of Patent: *Aug. 11, 2020

(54) MOTOR ASSEMBLY WITH HEAT EXCHANGER FOR CATHETER PUMP

(71) Applicant: TC1 LLC, St. Paul, MN (US)

(72) Inventors: Adam R. Tanner, Mountain View, CA (US); Michael R. Butler, Dublin, CA (US); Todd Jenkins, San Jose, CA (US)

(73) Assignee: TC1 LLC, St. Paul, MN (US)

(*) Notice: Subject to any disclaimer, the term of this patent is extended or adjusted under 35 U.S.C. 154(b) by 195 days.

This patent is subject to a terminal disclaimer.

(21) Appl. No.: 15/946,423

(22) Filed: Apr. 5, 2018

(65) Prior Publication Data

US 2018/0221551 A1 Aug. 9, 2018

Related U.S. Application Data

(63) Continuation of application No. 15/588,954, filed on May 8, 2017, now Pat. No. 9,987,404, which is a (Continued)

(51) Int. Cl.
*A61M 1/10* (2006.01)
*A61M 1/12* (2006.01)

(52) U.S. Cl.
CPC .......... *A61M 1/1029* (2014.02); *A61M 1/101* (2013.01); *A61M 1/1024* (2014.02);
(Continued)

(58) Field of Classification Search
CPC .............. A61M 1/1029; A61M 1/1036; A61M 1/1031; A61M 1/1024; A61M 1/101;
(Continued)

(56) References Cited

U.S. PATENT DOCUMENTS

| 1,902,418 A | 3/1933 | Pilgrim |
| 2,356,659 A | 8/1944 | De Paiva Aguiar |
| (Continued) | | |

FOREIGN PATENT DOCUMENTS

| CA | 2701810 A1 | 4/2009 |
| EP | 533432 A1 | 3/1993 |
| (Continued) | | |

OTHER PUBLICATIONS

Federal and Drug Administration 510(k) Summary for Predicate Device IMPELLA 2.5 (K112892), prepared on Sep. 5, 2012, 6 pp.
(Continued)

*Primary Examiner* — Mark Bockelman
(74) *Attorney, Agent, or Firm* — Armstrong Teasdale LLP

(57) ABSTRACT

A catheter pump is disclosed. The catheter pump can include an impeller and a catheter body having a lumen therethrough. The catheter pump can also include a drive shaft disposed inside the catheter body. A motor assembly can include a chamber. The motor assembly can include a rotor disposed in the at least a portion of the chamber, the rotor mechanically coupled with a proximal portion of the drive shaft such that rotation of the rotor causes the drive shaft to rotate. The motor assembly can also comprise a stator assembly disposed about the rotor. The motor assembly can also include a heat exchanger disposed about the stator assembly, the heat exchanger may be configured to direct heat radially outward away from the stator assembly, the rotor, and the chamber.

20 Claims, 10 Drawing Sheets

Related U.S. Application Data continuation of application No. 15/003,682, filed on Jan. 21, 2016, now Pat. No. 9,675,739.

(60) Provisional application No. 62/106,675, filed on Jan. 22, 2015.

(52) U.S. Cl.
CPC ........ *A61M 1/1031* (2014.02); *A61M 1/1034* (2014.02); *A61M 1/1036* (2014.02); *A61M 1/122* (2014.02); *A61M 1/125* (2014.02); *A61M 1/102* (2014.02); *A61M 1/1008* (2014.02); *A61M 1/1012* (2014.02); *A61M 2205/3317* (2013.01); *A61M 2205/3368* (2013.01); *A61M 2205/3606* (2013.01); *A61M 2205/3666* (2013.01)

(58) Field of Classification Search
CPC .... A61M 1/125; A61M 1/1034; A61M 1/122; A61M 1/102; A61M 1/1008; A61M 1/1012; A61M 2205/3317; A61M 2205/3368; A61M 2205/3666
See application file for complete search history.

(56) References Cited

U.S. PATENT DOCUMENTS

| | | | |
|---|---|---|---|
| 2,649,052 | A | 8/1953 | Weyer |
| 2,664,050 | A | 12/1953 | Abresch |
| 2,684,035 | A | 7/1954 | Kemp |
| 2,789,511 | A | 4/1957 | Doble |
| 2,896,926 | A | 7/1959 | Chapman |
| 2,935,068 | A | 5/1960 | Donaldson |
| 3,080,824 | A | 3/1963 | Boyd et al. |
| 3,455,540 | A | 7/1969 | Marcmann |
| 3,510,229 | A | 5/1970 | Smith |
| 3,812,812 | A | 5/1974 | Hurwitz |
| 3,860,968 | A | 1/1975 | Shapiro |
| 3,904,901 | A | 9/1975 | Renard et al. |
| 3,995,617 | A | 12/1976 | Watkins et al. |
| 4,115,040 | A | 9/1978 | Knorr |
| 4,129,129 | A | 12/1978 | Amrine |
| 4,135,253 | A | 1/1979 | Reich et al. |
| 4,143,425 | A | 3/1979 | Runge |
| 4,149,535 | A | 4/1979 | Volder |
| 4,304,524 | A | 12/1981 | Coxon |
| 4,382,199 | A | 5/1983 | Isaacson |
| 4,392,836 | A | 7/1983 | Sugawara |
| 4,458,366 | A | 7/1984 | MacGregor et al. |
| 4,540,402 | A | 9/1985 | Aigner |
| 4,560,375 | A | 12/1985 | Schulte et al. |
| 4,589,822 | A | 5/1986 | Clausen et al. |
| 4,625,712 | A | 12/1986 | Wampler |
| 4,655,745 | A | 4/1987 | Corbett |
| 4,686,982 | A | 8/1987 | Nash |
| 4,696,667 | A | 9/1987 | Masch |
| 4,704,121 | A | 11/1987 | Moise |
| 4,728,319 | A | 3/1988 | Masch |
| 4,753,221 | A | 6/1988 | Kensey et al. |
| 4,769,006 | A | 9/1988 | Papantonakos |
| 4,817,586 | A | 4/1989 | Wampler |
| 4,846,152 | A | 7/1989 | Wampler et al. |
| 4,895,557 | A | 1/1990 | Moise et al. |
| 4,900,227 | A | 2/1990 | Trouplin |
| 4,902,272 | A | 2/1990 | Milder et al. |
| 4,906,229 | A | 3/1990 | Wampler |
| 4,908,012 | A | 3/1990 | Moise et al. |
| 4,919,647 | A | 4/1990 | Nash |
| 4,944,722 | A | 7/1990 | Carriker et al. |
| 4,955,856 | A | 9/1990 | Phillips |
| 4,957,504 | A | 9/1990 | Chardack |
| 4,964,864 | A | 10/1990 | Summers et al. |
| 4,969,865 | A | 11/1990 | Hwang et al. |
| 4,976,270 | A | 12/1990 | Parl et al. |
| 4,985,014 | A | 1/1991 | Orejola |
| 4,994,017 | A | 2/1991 | Yozu |
| 4,995,857 | A | 2/1991 | Arnold |
| 5,000,177 | A | 3/1991 | Hoffmann et al. |
| 5,021,048 | A | 6/1991 | Buckholtz |
| 5,045,072 | A | 9/1991 | Castillo et al. |
| 5,049,134 | A | 9/1991 | Golding et al. |
| 5,061,256 | A | 10/1991 | Wampler |
| 5,089,016 | A | 2/1992 | Millner et al. |
| 5,092,844 | A | 3/1992 | Schwartz et al. |
| 5,098,256 | A | 3/1992 | Smith |
| 5,106,368 | A | 4/1992 | Uldall et al. |
| 5,112,200 | A | 5/1992 | Isaacson et al. |
| 5,112,292 | A | 5/1992 | Hwang et al. |
| 5,112,349 | A | 5/1992 | Summers et al. |
| 5,129,883 | A | 7/1992 | Black |
| 5,142,155 | A | 8/1992 | Mauze et al. |
| 5,147,186 | A | 9/1992 | Buckholtz |
| 5,163,910 | A | 11/1992 | Schwartz et al. |
| 5,169,378 | A | 12/1992 | Figuera |
| 5,171,212 | A | 12/1992 | Buck et al. |
| 5,190,528 | A | 3/1993 | Fonger et al. |
| 5,195,960 | A | 3/1993 | Hossain et al. |
| 5,201,679 | A | 4/1993 | Velte, Jr. et al. |
| 5,211,546 | A | 5/1993 | Isaacson et al. |
| 5,221,270 | A | 6/1993 | Parker |
| 5,234,407 | A | 8/1993 | Teirstein et al. |
| 5,234,416 | A | 8/1993 | Macaulay et al. |
| 5,290,227 | A | 3/1994 | Pasque |
| 5,300,112 | A | 4/1994 | Barr |
| 5,312,341 | A | 5/1994 | Turi |
| 5,344,443 | A | 9/1994 | Palma et al. |
| 5,346,458 | A | 9/1994 | Affeld |
| 5,360,317 | A | 11/1994 | Clausen et al. |
| 5,376,114 | A | 12/1994 | Jarvik |
| 5,393,197 | A | 2/1995 | Lemont et al. |
| 5,393,207 | A | 2/1995 | Maher et al. |
| 5,405,341 | A | 4/1995 | Martin |
| 5,405,383 | A | 4/1995 | Barr |
| 5,415,637 | A | 5/1995 | Khosravi |
| 5,437,541 | A | 8/1995 | Vainrub |
| 5,449,342 | A | 9/1995 | Hirose et al. |
| 5,458,459 | A | 10/1995 | Hubbard et al. |
| 5,490,763 | A | 2/1996 | Abrams et al. |
| 5,505,701 | A | 4/1996 | Anaya Fernandez de Lomana |
| 5,527,159 | A | 6/1996 | Bozeman, Jr. et al. |
| 5,533,957 | A | 7/1996 | Aldea |
| 5,534,287 | A | 7/1996 | Lukic |
| 5,554,114 | A | 9/1996 | Wallace et al. |
| 5,588,812 | A | 12/1996 | Taylor et al. |
| 5,609,574 | A | 3/1997 | Kaplan et al. |
| 5,613,935 | A | 3/1997 | Jarvik |
| 5,643,226 | A | 7/1997 | Cosgrove et al. |
| 5,678,306 | A | 10/1997 | Bozeman, Jr. et al. |
| 5,692,882 | A | 12/1997 | Bozeman, Jr. et al. |
| 5,702,418 | A | 12/1997 | Ravenscroft |
| 5,704,926 | A | 1/1998 | Sutton |
| 5,707,218 | A | 1/1998 | Maher et al. |
| 5,722,930 | A | 3/1998 | Larson, Jr. et al. |
| 5,725,513 | A | 3/1998 | Ju et al. |
| 5,725,570 | A | 3/1998 | Heath |
| 5,730,628 | A | 3/1998 | Hawkins |
| 5,735,897 | A | 4/1998 | Buirge |
| 5,738,649 | A | 4/1998 | Macoviak |
| 5,741,234 | A | 4/1998 | Aboul-Hosn |
| 5,741,429 | A | 4/1998 | Donadio, III et al. |
| 5,746,709 | A | 5/1998 | Rom et al. |
| 5,749,855 | A | 5/1998 | Reitan |
| 5,755,784 | A | 5/1998 | Jarvik |
| 5,776,111 | A | 7/1998 | Tesio |
| 5,776,161 | A | 7/1998 | Globerman |
| 5,776,190 | A | 7/1998 | Jarvik |
| 5,779,721 | A | 7/1998 | Nash |
| 5,807,311 | A | 9/1998 | Palestrant |
| 5,814,011 | A | 9/1998 | Corace |
| 5,824,070 | A | 10/1998 | Jarvik |
| 5,851,174 | A | 12/1998 | Jarvik et al. |
| 5,859,482 | A | 1/1999 | Crowell et al. |
| 5,868,702 | A | 2/1999 | Stevens et al. |

(56) References Cited

U.S. PATENT DOCUMENTS

| | | |
|---|---|---|
| 5,868,703 A | 2/1999 | Bertolero et al. |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III |
| 6,053,705 A | 4/2000 | Schoeb et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,093,001 A | 7/2000 | Burgreen et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,178,922 B1 | 1/2001 | Denesuk et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,503,224 B1 | 1/2003 | Forman et al. |
| 6,508,777 B1 | 1/2003 | Macoviak et al. |
| 6,508,787 B2 | 1/2003 | Erbel Reimund et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | Deblanc et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,860,713 B2 | 3/2005 | Hoover |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser Peter et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez et al. |
| 7,605,298 B2 | 10/2009 | Bechert et al. |

(56) References Cited

U.S. PATENT DOCUMENTS

| | | |
|---|---|---|
| 7,619,560 B2 | 11/2009 | Penna et al. |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado, III et al. |
| 8,025,647 B2 | 9/2011 | Siess et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung et al. |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan et al. |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans et al. |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 9,381,288 B2 | 7/2016 | Schenck et al. |
| 9,421,311 B2 | 8/2016 | Tanner et al. |
| 9,446,179 B2 | 9/2016 | Keenan et al. |
| 2002/0107506 A1 | 8/2002 | McGuckin et al. |
| 2003/0018380 A1 | 1/2003 | Craig et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0137680 A1 | 6/2005 | Ortiz et al. |
| 2005/0165269 A9 | 7/2005 | Aboul-Hosn et al. |
| 2005/0250975 A1 | 11/2005 | Carrier et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0156006 A1 | 7/2007 | Smith et al. |
| 2008/0004645 A1 | 1/2008 | To et al. |
| 2008/0103442 A1 | 5/2008 | Kesten et al. |
| 2008/0103516 A1 | 5/2008 | Wulfman et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0275290 A1 | 11/2008 | Viole et al. |
| 2009/0018567 A1 | 1/2009 | Escudero et al. |
| 2009/0024085 A1 | 1/2009 | To et al. |
| 2009/0099638 A1 | 4/2009 | Grewe |
| 2009/0112312 A1 | 4/2009 | LaRose et al. |
| 2009/0118567 A1 | 5/2009 | Siess |
| 2009/0182188 A1 | 7/2009 | Marseille et al. |
| 2009/0234378 A1 | 9/2009 | Escudero et al. |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0127871 A1 | 5/2010 | Pontin |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2010/0286791 A1 | 11/2010 | Goldsmith |
| 2011/0004046 A1 | 1/2011 | Campbell et al. |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0237863 A1 | 9/2011 | Ricci et al. |
| 2011/0257462 A1 | 10/2011 | Rodefeld et al. |
| 2012/0004495 A1 | 1/2012 | Bolling et al. |
| 2012/0029265 A1 | 2/2012 | Larose et al. |
| 2012/0059213 A1 | 3/2012 | Spence et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0178985 A1 | 7/2012 | Walters et al. |
| 2012/0178986 A1 | 7/2012 | Campbell et al. |
| 2012/0184803 A1 | 7/2012 | Simon et al. |

(56) References Cited

U.S. PATENT DOCUMENTS

| | | |
|---|---|---|
| 2012/0203056 A1 | 8/2012 | Corbett |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0245404 A1 | 9/2012 | Smith et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0066140 A1 | 3/2013 | McBride et al. |
| 2013/0085318 A1 | 4/2013 | Toellner |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz Heike et al. |
| 2014/0067057 A1 | 3/2014 | Callaway et al. |
| 2014/0088455 A1 | 3/2014 | Christensen et al. |
| 2014/0148638 A1 | 5/2014 | Larose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Scheckel et al. |

FOREIGN PATENT DOCUMENTS

| | | |
|---|---|---|
| EP | 1207934 A2 | 5/2002 |
| EP | 1393762 A1 | 3/2004 |
| EP | 1591079 A1 | 11/2005 |
| EP | 2263732 A2 | 12/2010 |
| EP | 2298374 A1 | 3/2011 |
| FR | 2267800 A1 | 11/1975 |
| GB | 2239675 A | 7/1991 |
| JP | S48-23295 | 3/1973 |
| JP | H06114101 A | 4/1994 |
| JP | H10099447 | 4/1998 |
| TW | 500877 B | 9/2002 |
| WO | 8905164 A1 | 6/1989 |
| WO | 9526695 A2 | 10/1995 |
| WO | 9715228 A1 | 5/1997 |
| WO | 9737697 A1 | 10/1997 |
| WO | 12148 | 3/2000 |
| WO | 19097 A1 | 4/2000 |
| WO | 43062 A1 | 7/2000 |
| WO | 61207 A1 | 10/2000 |
| WO | 69489 A1 | 11/2000 |
| WO | 117581 A2 | 3/2001 |
| WO | 0119444 A1 | 3/2001 |
| WO | 124867 A1 | 4/2001 |
| WO | 2070039 A2 | 9/2002 |
| WO | 3103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2011076439 A1 | 6/2010 |
| WO | 2010127871 A1 | 11/2010 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011089022 A1 | 7/2011 |
| WO | 2012007140 | 1/2012 |
| WO | 2012007141 | 1/2012 |
| WO | 2013148697 A1 | 10/2013 |
| WO | 2013160407 A1 | 10/2013 |
| WO | 2014019274 A1 | 2/2014 |
| WO | 2015063277 A3 | 7/2015 |

OTHER PUBLICATIONS

Extended European Search Report received in European Patent Application No. 14 779928.2, dated Oct. 7, 2016, in 6 pages. (THOR.084EP).

Extended European Search Report received in European Patent Application No. 14 764392.8, dated Oct. 27, 2016, in 7 pages. (THOR.097EP).

International Search Report and Written Opinion received in International Patent Application No. PCT/US2016/014379, dated Jul. 25, 2016, in 19 pages (THOR.128WO).

Schmitz-Rode et al., "Axial flow catheter pump for circulatory support," Biomedizinische Technik, 2002, Band 4 7, Erganzungsband 1, Tei I 1, pp. 142-143.

Abiomed, "Impella 5.0 with the Impella Console, Circulatory Support System, Instructions for Use & Clinical Reference Manual," Jun. 2010, in 122 pages.

ABIOMED—Recovering Hearts. Saving Lives., Impella 2.5 System, Instructions for Use, Jul. 2007, in 86 sheets.

Aboul-Hosn et al., "The Hemopump: Clinical Results and Future Applications", Assisted Circulation 4, 1995, in 14 pages.

Barras et al., "Nitinol—Its Use in Vascular Surgery arid Other Applications," Eur. J. Vase. Endovasc. Surg., 2000, pp. 564-569; vol. 19.

Biscarini et al., "Enhanced Nitinol Properties for Biomedical Applications," Recent Patents on Biomedical Engineering, 2008, pp. 180-196, vol. 1 (3).

Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.

Compendium of Technical and Scientific Information for the HEMOPUMP Temporary Cardiac Assist System, Johnson & Johnson Interventional Systems, 1988, in 15 pages.

Dekker et al., "Efficacy of a New Intraaortic Propeller Pump vs the Intraaortic Balloon Pump*, An Animal Study", Chest, Jun. 2003, vol. 123, No. 6, pp. 2089-2095.

Duerig et al., "An Overview of Nitinol Medical Applications," Materials Science Engineering, 1999, pp. 149-160; vol. A273.

European Search Report received in European Patent Application No. 05799883.3, dated May 10, 2011, in 4 pages.

Extended European Search Report received in European Patent Application No. 07753903.9, dated Oct. 8, 2012, in 7 pages (THOR.034VEP).

Grech, "Percutaneous Coronary Intervention, I: History and Development," BMJ., May 17, 2003, pp. 1080-1082; vol. 326.

Hsu et al., "Review of Recent Patents on Foldable Ventricular Assist Devices," Recent Patents on Biomedical Engineering, 2012, pp. 208-222, vol. 5.

(56) References Cited

OTHER PUBLICATIONS

Ide et al., "Evaluation of the Pulsatility of a New Pulsatile Left Ventricular Assist Device—the integrated Cardioassist Catheter-in Dogs," J. of Thorac and Cardiovasc Sur, Feb. 1994, pp. 569-0575, vol. 107(2).

Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).

Impella CP®—Instructions for Use & Clinical Reference Manual (United States only), Abiomed, Inc.; Jul. 2014, 148 pages, www.abiomed.com.

Impella LD® with the Impella® Controller—Circulatory Support System—Instructions for Use & Clinical Reference Manual (United States only), Abiomed, Inc., Sep. 2010, 132 pages, www.abiomed.com.

International Preliminary Examination Report received in International Patent Application No. PCT/US2003/04853, dated Jul. 26, 2004, in 5 pages.

International Preliminary Examination Report received in International Patent Application No. PCT/US2003/04401, dated May 18, 2004, in 4 pages.

International Preliminary Report on Patentability and Written Opinion of the International Searching Authority received in International Patent Application No. PCT/US2005/033416, dated Mar. 20, 2007, in 7 pages.

International Preliminary Report on Patentability and Written Opinion of the International Searching Authority received in International Patent Application No. PCT/US2007/007313, dated Sep. 23, 2008, in 6 pages.

International Preliminary Report on Patentability and Written Opinion received in International Patent Application No. PCT/US2014/020878, dated Sep. 15, 2015, in 8 pages.

International Search Report and Written Opinion received in International Patent Application No. PCT/US2005/033416, dated Dec. 11, 2006, in 8 pages.

International Search Report and Written Opinion received in International Patent Application No. PCT/US2007/007313, dated Mar. 4, 2008, in 6 pages.

International Search Report and Written Opinion received in International Patent Application No. PCT/US2012/020382, dated Jul. 31, 2012, in 11 pages.

International Search Report and Written Opinion received in International Patent Application No. PCT/US2012/020369, dated Jul. 30, 2012, in 10 pages.

International Search Report and Written Opinion received in International Patent Application No. PCT/US2012/020553, dated Aug. 17, 2012, in 8 pages.

International Search Report and Written Opinion received in International Patent Application No. PCT/US2012/020383, dated Aug. 17, 2012; in 9 pages.

International Search Report and Written Opinion received in International Patent Application No. PCT/US2013/040798, dated Aug. 21, 2013, in 16 pages.

International Search Report and Written Opinion received in International Patent Application No. PCT/US2013/040799, dated Aug. 21, 2013, in 19 pages.

International Search Report and Written Opinion received in International Patent Application No. PCT/US2013/040809, dated Sep. 2, 2013, in 25 pages.

International Search Report and Written Opinion received in International Patent Application No. PCT/US2013/048332, dated Oct. 16, 2013, in 17 pages.

International Search Report and Written Opinion received in International Patent Application No. PCT/US2013/048343, dated Oct. 11, 2013, in 15 pages.

International Search Report and Written Opinion received in International Patent Application No, PCT/US2014/020878, dated May 7, 2014, in 13 pages.

International Search Reort and Written Opinion received in International Patent Application No. PCT/US2015/026013, dated Jul. 8, 2015, in 12 pages.

International Search Report and Written Opinion received in International Patent Application No. PCT/US2015/026014, dated Jul. 15, 2015, in 13 pages.

International Search Report and Written Opinion received in International Patent Application No. PCT/US2015/026025, dated Jul. 20, 2015, in 12 pages.

International Search Report and Written Opinion received in International Patent Application No. PCT/US2015/025959, dated Aug. 28, 2015, in 16 pages.

International Search Report and Written Opinion received in International Patent Application No. PCT/US2015/025960, dated Sep. 3, 2015, in 15 pages.

International Search Report and Written Opinion received in International Patent Application No. PCT/US2015/045370, dated Nov. 18, 2015, in 12 pages.

International Search Report received in International Patent Application No. PCT/US2003/004401, dated Nov. 10, 2003, in 9 pages.

International Search Report received in International Patent Application No. PCT/US2003/004353, dated Jul. 3, 2003, in 3 pages.

International Search Report Written Opinion received in International Patent Application No. PCT/US2010/040847, dated Dec. 14, 2010, in 17 pages.

International Search Report and Written Opinion received in International Patent Application No. PCT/US2014/020790, dated Aug. 6, 2014, in 12 pages.

JOMED Reitan Catheter Pump RCP, Percutaneous Circulatory Support, in 10 pages, believed to be published prior to Oct. 15, 2003.

JOMED Reitan Catheter Pump RCP, Feb. 18, 2003, in 4 pages.

Krishnamani et al., "Emerging Ventricular Assist Devices for Long-Term Cardiac Support," National Review, Cardiology, Feb. 2010, pp. 71-76, vol. 7.

Kunst et al., "Integrated unit for programmable control of the 21 F Hemopump and registration of physiological signals," Medical & Biological Engineering & Computing, Nov. 1994, pp. 694-696.

Mihaylov et al., "Development of a New Introduction Technique for the Pulsatile Catheter Pump," Artificial Organs, 1997, pp. 425-427; vol. 21 (5).

Mihaylov et al., "Evaluation of the Optimal Driving Mode During Left Ventricular Assist with Pulsatile Catheter Pump in Calves," Artificial Organs, 1999, pp. 1117-1122; vol. 23(12).

Minimally Invasive Cardiac Assist JOMED Catheter PumpTM, in 6 pages, believed to be published prior to Jun. 16, 1999.

Morgan, "Medical Shape Memory Alloy Applications—The Market and its Products," Materials Science and Engineering, 2004, pp. 16-23, vol. A 378.

Morsink et al., "Numerical Modelling of Blood Flow Behaviour in the Valved Catheter of the PUCA-Pump, a LVAD," The International Journal of Artificial Organs, 1997, pp. 277-284; vol. 20(5).

Nishimura et al, "The Enabler Cannula Pump: A Novel Circulatory Support System," The International Journal of Artificial Organs, 1999, pp. 317-323; vol. 22(5).

Petrini et al., "Biomedical Applications of Shape Memory Alloys," Journal of Metallurgy, 2011, pp. 1-15.

Raess et al., "Impella 2.5," J. Cardiovasc. Transl. Res., 2009, pp. 168-172, vol. 2(2).

Rakhorst et al., "In Vitro Evaluation of the Influence of Pulsatile Intraventricular Pumping on Ventricular Pressure Patterns," Artificial Organs, 1994, pp. 494-499, vol. 18(7).

Reitan, Evaluation of a New Percutaneous Cardiac Assist Device, Department of Cardiology, Faculty of Medicine, Lund University, Sweden, 2002, in 172 pages.

Reitan et al., "Hemodynamic Effects of a New Percutaneous Circulatory Support Device in a Left Ventricular Failure Model," ASAIO Journal, 2003, pp. 731-736, vol. 49.

Reitan et al., "Hydrodynamic Properties of a New Percutaneous Intra-Aortic Axial Flow Pump," ASAIO Journal2000, pp. 323-328.

Rothman, "The Reitan Catheter Pump: A New Versatile Approach for Hemodynamic Support", London Chest Hospital Barts &

(56) References Cited

OTHER PUBLICATIONS

The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Siess et al., "Hydraulic refinement of an intraarterial microaxial blood pump", The International Journal of Artificial Organs, 1995, vol. 18, No. 5, pp. 273-285.
Siess, "Systemanalyse und Entwicklung intravasaler Rotationspumpen zur Herzunterstlitzung", Helmholtz-Institut fur Blomedixinische Technik an der RWfH Aachen, Jun. 24, 1998, in 105 pages.
Siess et al., "Basic design criteria for rotary blood pumps," H. Masuda, Rotary Blood Pumps, Springer, Japan,2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1 (4).
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./ Sep. 2009.
Written Opinion received in International Patent Application No. PCT/US2003/04853, dated Feb. 25, 2004, 5 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 6 pages.
International Search Report and Written Opinion received in International Patent Application No. PCT/US2016/014371, dated May 2, 2016, in 18 pages.
International Search Report and Written Opinion received in International Patent Application No. PCT/US2016/014391, dated May 2, 2016, in 17 pages.
Nullity Action against the owner of the German part DE 50 2007 005 015.6 of European patent EP 2 04 7 872 81, dated Jul. 13, 2015, in 61 pages.
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Extended EP Search Report, dated Dec. 13, 2019, for EP patent application No. EP 19195969.1 (4 pgs.).

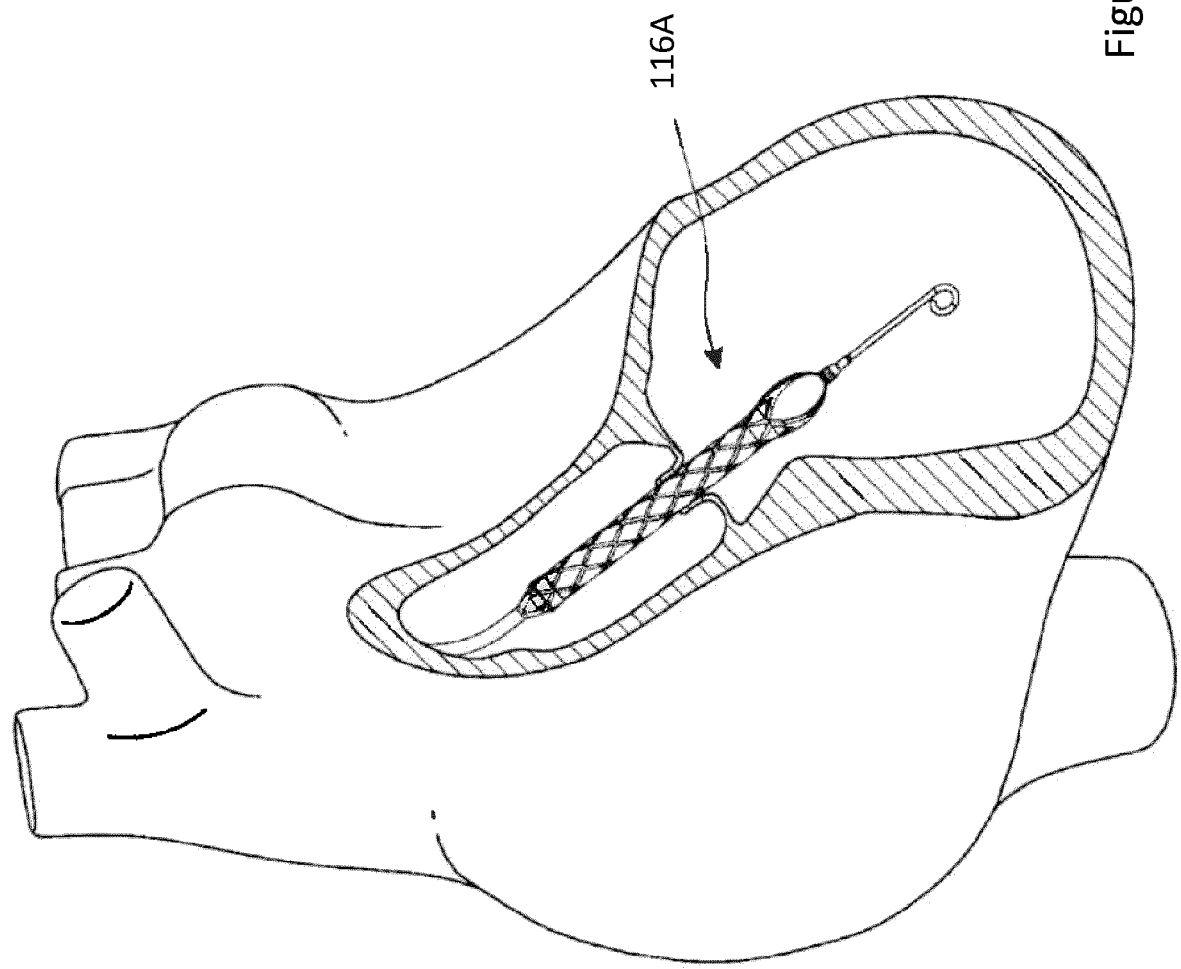

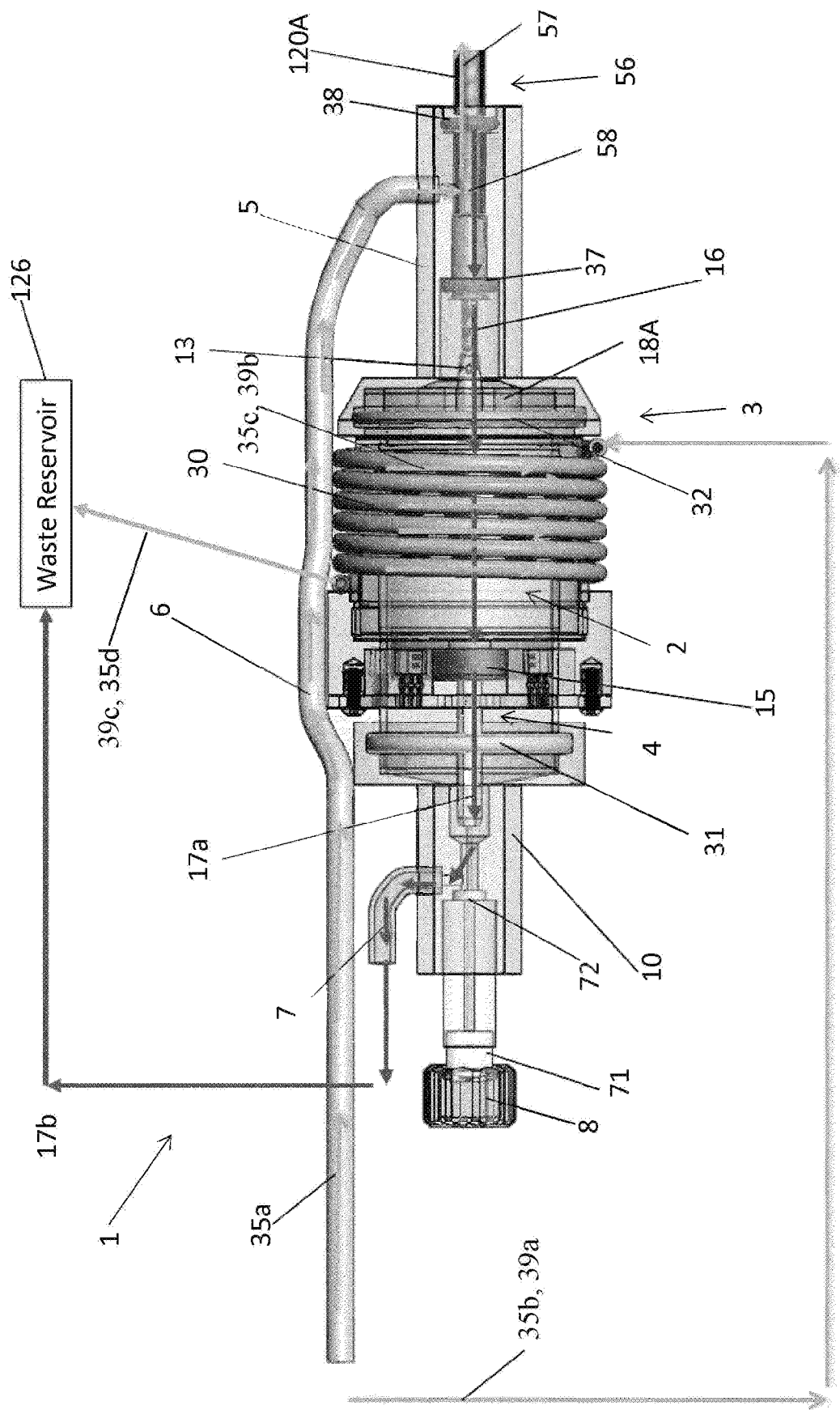

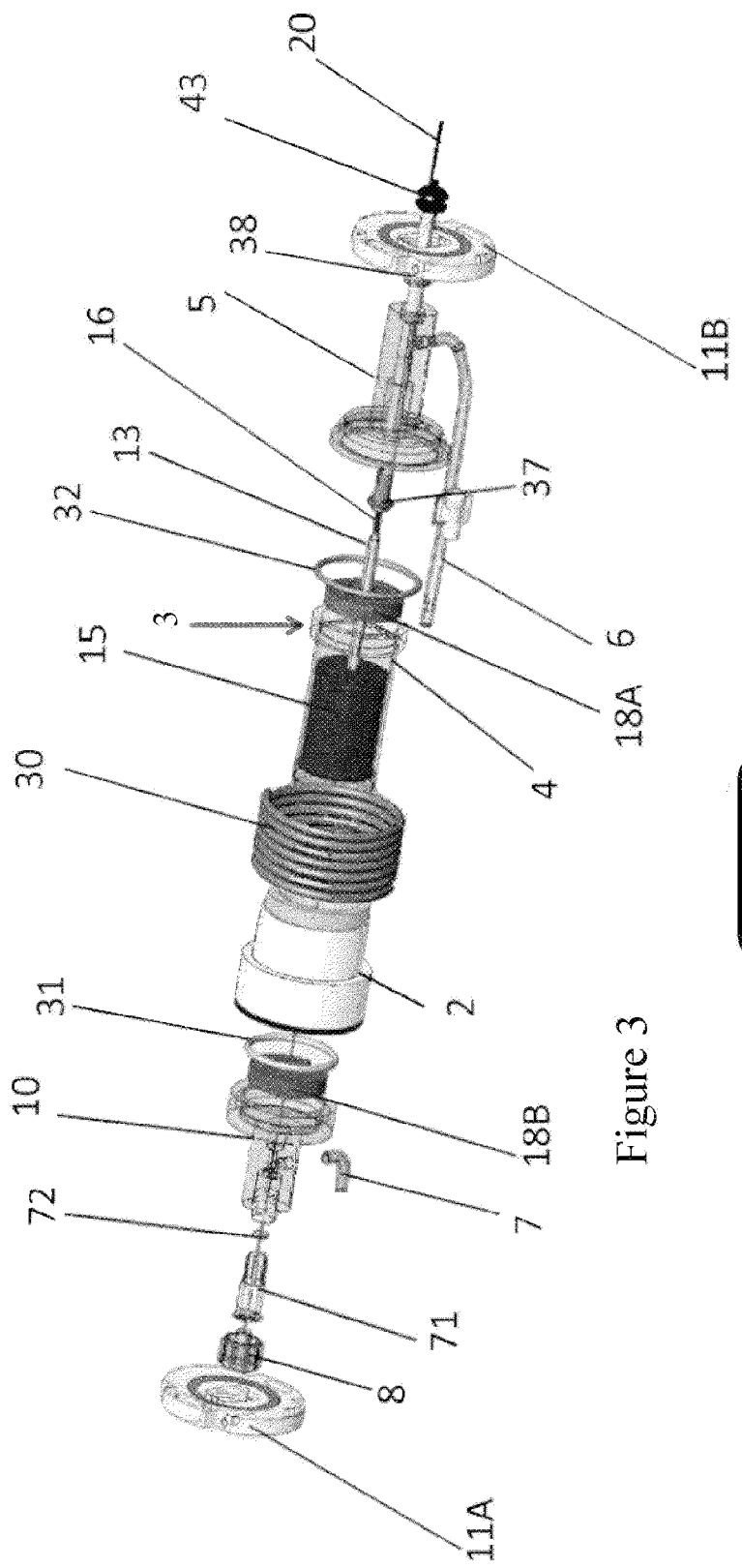
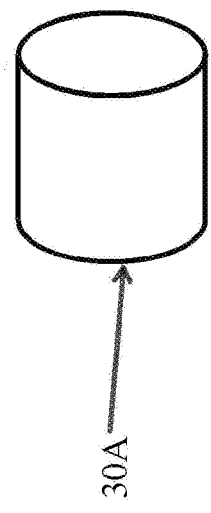
Figure 3
Figure 3A

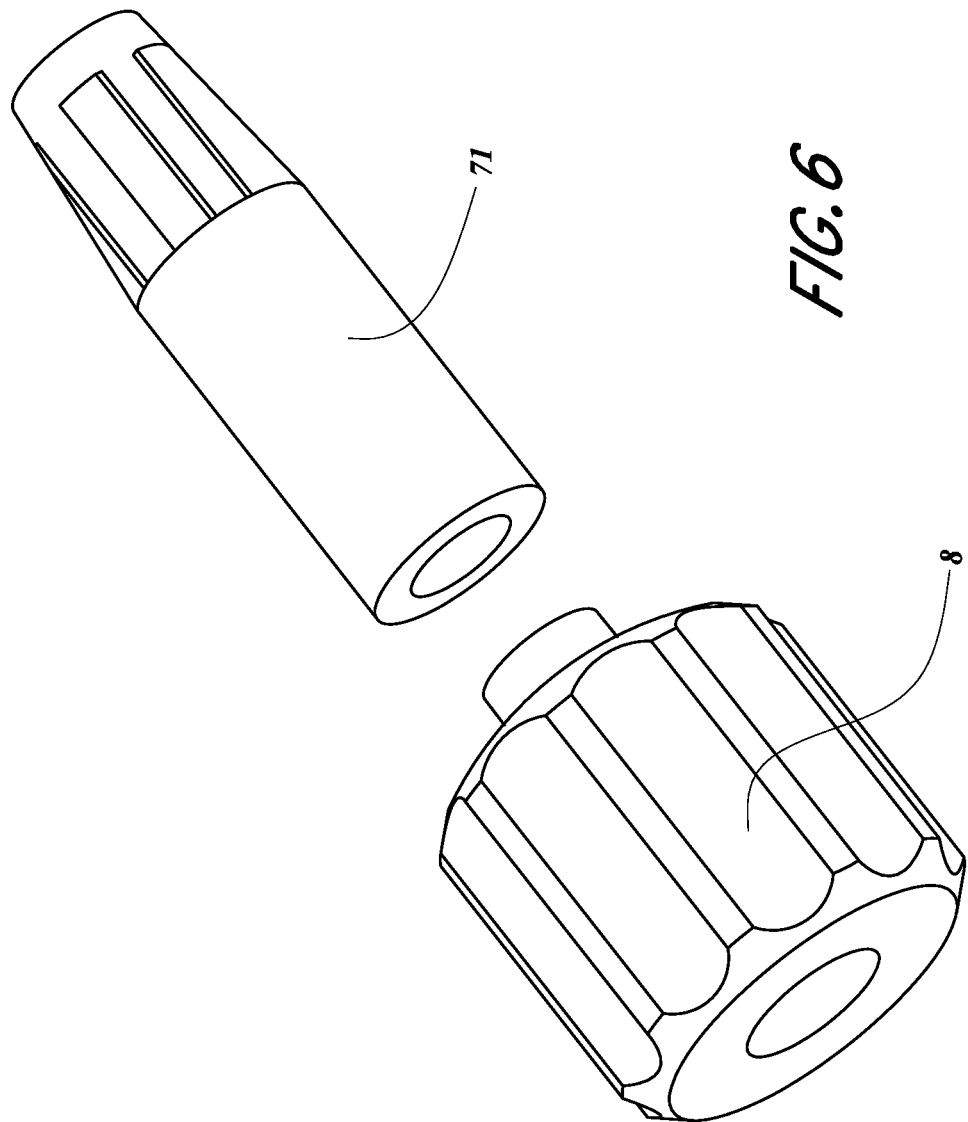

MOTOR ASSEMBLY WITH HEAT EXCHANGER FOR CATHETER PUMP

CROSS-REFERENCE TO RELATED APPLICATIONS

This application is a Continuation of U.S. patent application Ser. No. 15/588,954, filed on May 8, 2017, now issued U.S. Pat. No. 9,987,404, which is a Continuation of U.S. patent application Ser. No. 15/003,682, filed Jan. 21, 2016, now issued U.S. Pat. No. 9,675,739, which claims priority to U.S. Provisional Patent Application No. 62/106,675, filed on Jan. 22, 2015, the entire contents of which are hereby incorporated by reference herein for all purposes.

BACKGROUND OF THE INVENTION

Field of the Invention

This application is directed to catheter pumps for mechanical circulatory support of a heart.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Mechanical circulatory support (MCS) systems and ventricular assist devices (VADs) have gained greater acceptance for the treatment of acute heart failure, such as to stabilize a patient after cardiogenic shock, during treatment of acute myocardial infarction (MI) or decompensated heart failure, or to support a patient during high risk percutaneous coronary intervention (PCI). An example of an MCS system is a rotary blood pump placed percutaneously, e.g., via a catheter without a surgical cutdown.

In a conventional approach, a blood pump is inserted into the body and connected to the cardiovascular system, for example, to the left ventricle and the ascending aorta to assist the pumping function of the heart. Other known applications include pumping venous blood from the right ventricle to the pulmonary artery for support of the right side of the heart. Typically, acute circulatory support devices are used to reduce the load on the heart muscle for a period of time, to stabilize the patient prior to heart transplant or for continuing support.

There is a need for improved mechanical circulatory support devices for treating acute heart failure. There is a need for devices designed to provide near full heart flow rate and inserted percutaneously (e.g., through the femoral artery without a cutdown).

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events.

In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure.

While the flow rate of a rotary pump can be increased by rotating the impeller faster, higher rotational speeds are known to increase the risk of hemolysis, which can lead to adverse outcomes and in some cases death. Higher speeds also lead to performance and patient comfort challenges. Many percutaneous ventricular assist devices (VADs) have driveshafts between the motor and impeller rotating at high speeds. Some percutaneous VADs are designed to rotate at speeds of more than 15,000 RPM, and in some case more than 25,000 RPM in operation. The vibration, noise, and heat from the motor and driveshaft can cause discomfort to the patient when positioned, especially when positioned inside the body. Accordingly, there is a need to for a device that improves performance and patient comfort with a high speed motor.

There is a need for a motor configured to drive an operative device, e.g., an impeller, at a distal portion of the pump. It can be important for the motor to be configured to allow for percutaneous insertion of the pump's impeller.

These and other problems are overcome by the inventions described herein.

SUMMARY OF THE INVENTION

There is an urgent need for a pumping device that can be inserted percutaneously and also provide full cardiac rate flows of the left, right, or both the left and right sides of the heart when called for.

In one embodiment, a catheter pump system is disclosed. The catheter pump system can include an impeller and a catheter body having a lumen therethrough. The catheter pump system can include a drive shaft disposed inside the catheter body and coupled with the impeller at a distal portion of the drive shaft. The catheter pump system can include a motor assembly comprising a rotor mechanically coupled with a proximal portion of the drive shaft. The catheter pump system can include a heat exchanger coupled with the motor assembly to remove heat therefrom, the heat exchanger comprising a volume to receive fluid.

In another embodiment, a catheter pump system is disclosed. The catheter pump system can include an impeller and a catheter body having a lumen therethrough. The catheter pump system can include a drive shaft disposed inside the catheter body and coupled with the impeller at a distal portion of the drive shaft, the drive shaft configured such that rotation of the drive shaft causes the impeller to rotate. The catheter pump system can include a motor assembly. The motor assembly can include a motor housing and a chamber disposed in the motor housing, at least a portion of the chamber in fluid communication with the lumen of the catheter body. The motor assembly can include a damper configured to reduce the transmission of vibrations from the motor assembly.

In yet another embodiment, a catheter pump system is disclosed. The catheter pump system can include an impeller and a catheter body having a lumen therethrough, the impeller mechanically coupled with a distal portion of the catheter body. The catheter pump system can include a guidewire guide tube disposed through the lumen from a proximal portion of the catheter pump to a distal portion of the catheter pump, the guidewire guide tube configured to receive a guidewire therein. The catheter pump system can include an end cap secured to a proximal end portion of the guide tube, the end cap configured such that axial movement of the end cap relative to the catheter body causes the guidewire guide tube to be removed from the catheter pump. The catheter pump system can include a resealable closure device disposed at a proximal portion of the catheter pump, the closure device configured such that when the guidewire guide tube is removed from the catheter pump, the closure device encloses the proximal portion of the catheter pump.

In another embodiment, a catheter pump system is disclosed. The catheter pump system can include an impeller and a catheter body having a lumen therethrough. The catheter pump system can include a drive shaft disposed inside the catheter body and coupled with the impeller at a distal portion of the drive shaft. The catheter pump system can include a motor assembly. The motor assembly can comprise a housing and a stator assembly within the housing. The motor assembly can comprise a rotor positioned within the stator assembly, the rotor commutated by the stator, the rotor connected to a proximal portion of the drive shaft. The motor assembly can comprise a thermal layer disposed within the housing and configured to transfer heat away from the stator and/or the rotor.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 1A illustrates one embodiment of a catheter pump with an impeller assembly configured for percutaneous application and operation.

FIG. 2B is a side plan view of the motor assembly of the catheter pump system shown in FIG. 1B, according to another embodiment.

FIG. 3 is a perspective exploded view of a portion of the motor assemblies shown in FIGS. 2A-2C.

FIG. 3A is a schematic view of a heat exchanger, according to another embodiment.

FIG. 6 is an image of a cap and a female receiver for releasably securing a guide tube in a lumen that extends through the motor assembly of FIG. 4, with the guide tube not shown.

More detailed descriptions of various embodiments of components for heart pumps useful to treat patients experiencing cardiac stress, including acute heart failure, are set forth below.

DETAILED DESCRIPTION

This application is generally directed to apparatuses for inducing motion of a fluid relative to the apparatus. Exemplars of circulatory support systems for treating heart failure, and in particular emergent and/or acute heart failure, are disclosed in U.S. Pat. Nos. 4,625,712; 4,686,982; 4,747,406; 4,895,557; 4,944,722; 6,176,848; 6,926,662; 7,022,100; 7,393,181; 7,841,976; 8,157,719; 8,489,190; 8,597,170; 8,721,517 and U.S. Pub. Nos. 2012/0178986 and 2014/0010686, the entire contents of which patents and publications are incorporated by reference for all purposes. In addition, this application incorporates by reference in its entirety and for all purposes the subject matter disclosed in each of the following concurrently filed applications and the provisional applications to which they claim priority: application Ser. No. 15/635,531, entitled "REDUCED ROTATIONAL MASS MOTOR ASSEMBLY FOR CATHETER PUMP," filed on Jun. 28, 2017 and claiming priority to U.S. Provisional Patent Application No. 62/106,670; and application Ser. No. 15/003,696, now U.S. Pat. No. 9,675,738, entitled "ATTACHMENT MECHANISMS FOR MOTOR OF CATHETER PUMP," filed on Jan. 21, 2016 and claiming priority to U.S. Provisional Patent Application No. 62/106,673.

In one example, an impeller can be coupled at a distal portion of the apparatus. Some embodiments generally relate to various configurations for a motor assembly adapted to drive an impeller at a distal end of a catheter pump, e.g., a percutaneous heart pump. In such applications, the disclosed motor assembly is disposed outside the patient in some embodiments. In other embodiments, the disclosed motor assembly and/or features of the motor are miniaturized and sized to be inserted within the body, e.g., within the vasculature.

Figure 1B:
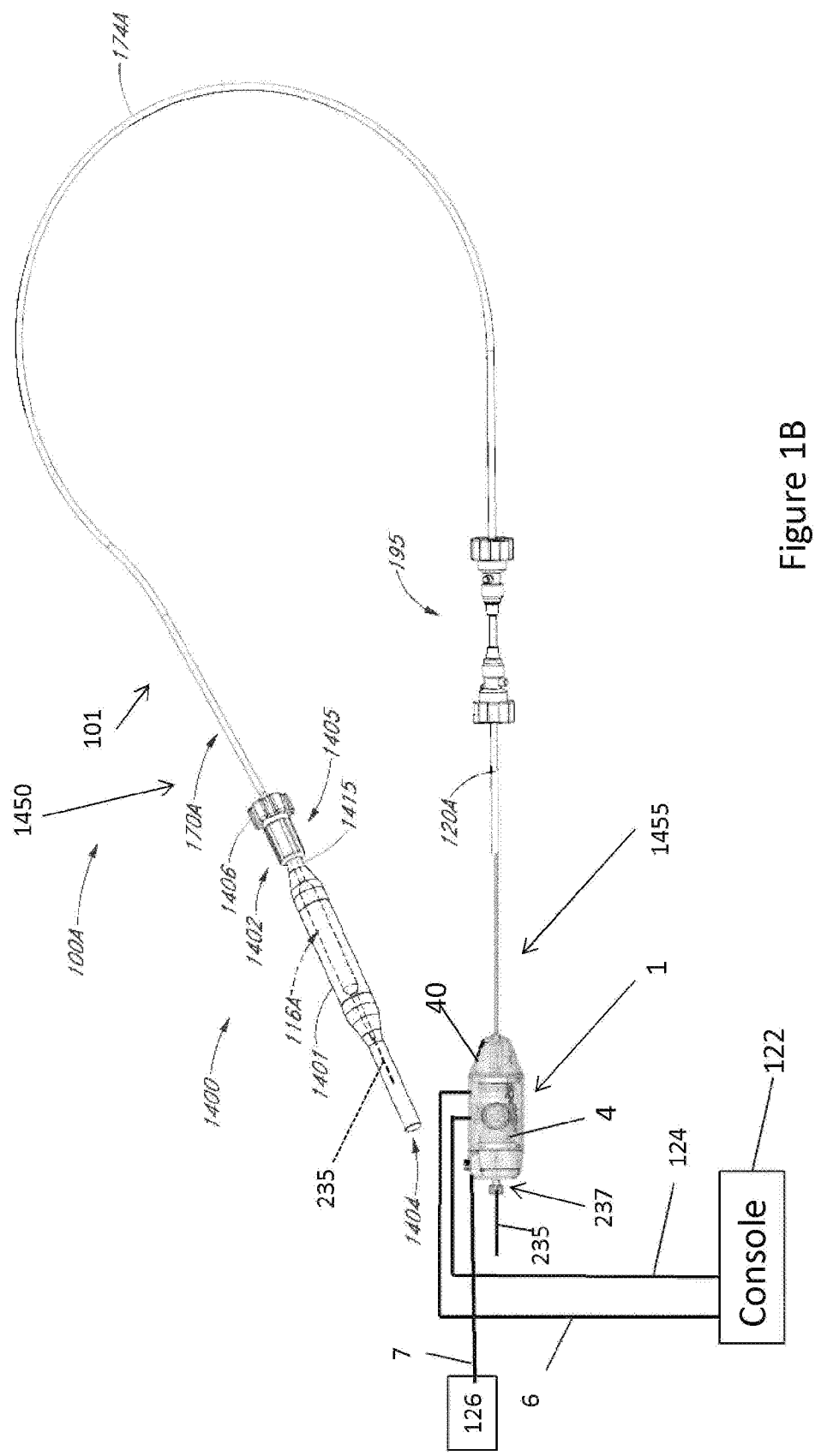
FIG. 1B is a schematic view of one embodiment of a catheter pump system adapted to be used in the manner illustrated in FIG. 1A.

FIGS. 1A-1B show aspects of an exemplary catheter pump 100A that can provide high performance, e.g., high blood flow rates. As shown in FIG. 1B, the pump 100A includes a motor assembly 1 driven by a console 122, which can include an electronic controller and various fluid handling systems. The console 122 directs the operation of the motor 1 and an infusion system that supplies a flow of fluid (e.g., saline) in the pump 100A. Additional details regarding the console 122 may be found throughout U.S. Patent Publication No. US 2014/0275725, the contents of which are incorporated by reference herein in their entirety and for all purposes.

The pump 100A includes a catheter assembly that can be coupled with the motor assembly 1 and can house an impeller in an impeller assembly 116A within a distal portion of the catheter assembly of the pump 100A. In various embodiments, the impeller is rotated remotely by the motor 1 when the pump 100A is operating. For example, the motor 1 can be disposed outside the patient. In some embodiments, the motor 1 is separate from the console 122, e.g., to be placed closer to the patient. In the exemplary system the pump is placed in the patient in a sterile environment and the console is outside the sterile environment. In one embodiment, the motor is disposed on the sterile side of the system. In other embodiments, the motor 1 is part of the console 122.

Figure 1C:
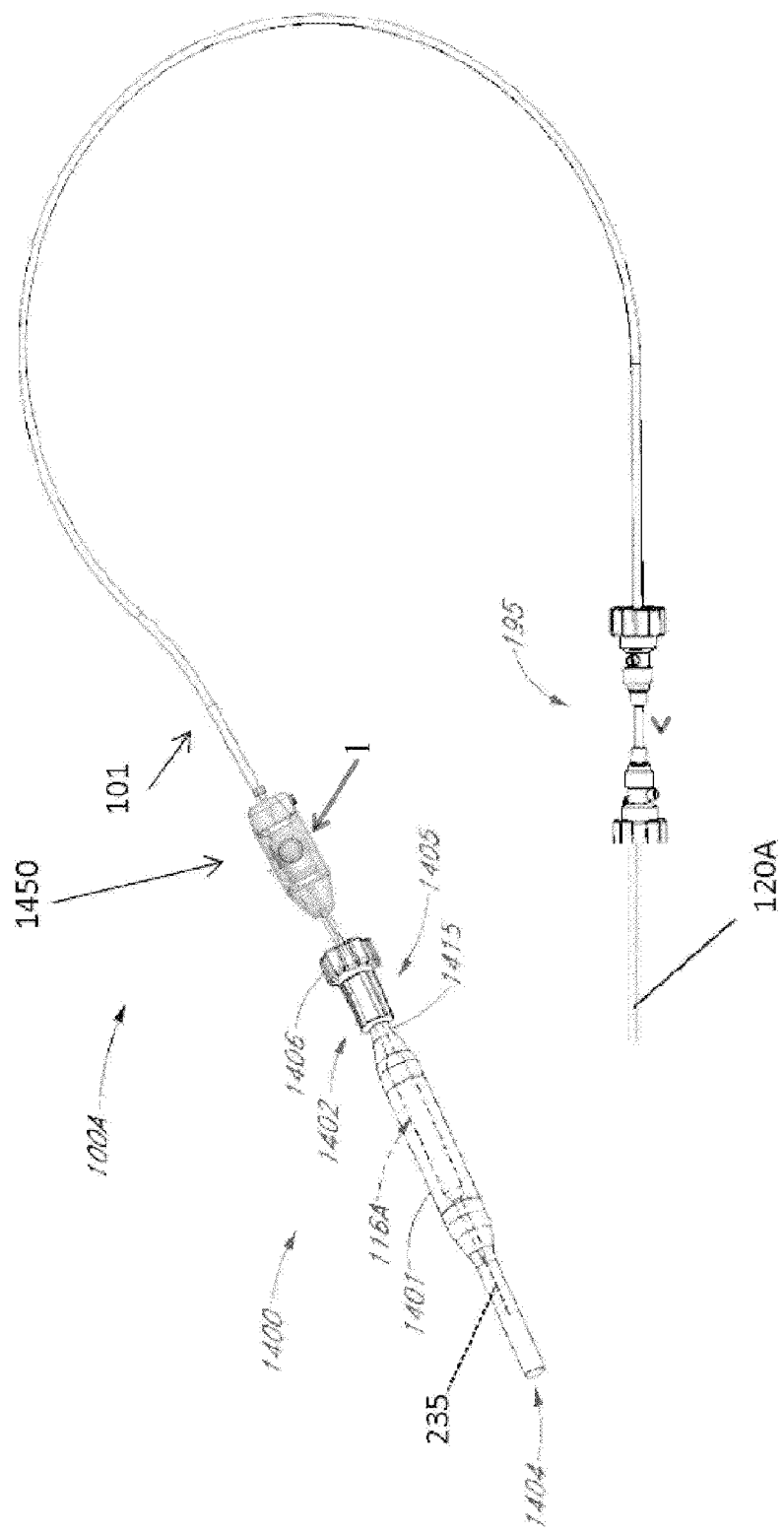
FIG. 1C is a schematic view of another embodiment of a catheter pump system.

In still other embodiments, the motor is miniaturized to be insertable into the patient. For example, FIG. 1C is a schematic view of another embodiment of a catheter pump system. FIG. 1C is similar to FIG. 1B, except the motor 1 is miniaturized for insertion into the body. As shown in FIG. 1C, for example, the motor 1 can be disposed proximal the impeller assembly 116A. The motor 1 can be generally similar to the motor assembly shown in FIGS. 2A-2C, except the motor 1 is sized and shaped to be inserted into the patient's vasculature. One or more electrical lines may extend from the motor to the console outside the patient. The electrical lines can send signals for controlling the operation of the motor. Such embodiments allow a drive shaft coupled with the impeller and disposed within the catheter assembly to be much shorter, e.g., shorter than the distance from the aortic valve to the aortic arch (about 5 cm or less). Some examples of miniaturized motor catheter pumps and related components and methods are discussed in U.S. Pat. Nos. 5,964,694; 6,007,478; 6,178,922; and 6,176,848, all of which are hereby incorporated by reference herein in their entirety for all purposes. Various embodiments of the motor assembly 1 are disclosed herein, including embodiments having a rotor disposed within a stator assembly. In various embodiments, waste fluid can pass through a housing 4 in which the rotor is disposed to help cool the motor assembly 1.

FIG. 1A illustrates one use of the catheter pump 100A. A distal portion of the pump 100A including a catheter assembly including the impeller assembly 116A is placed in the left ventricle LV of the heart to pump blood from the LV into the aorta. The pump 100A can be used in this way to treat a wide range of heart failure patient populations including, but not limited to, cardiogenic shock (such as acute myocardial infarction, acute decompensated heart failure, and postcardiotomy), myocarditis, and others. The pump can also be used for various other indications including to support a patient during a cardiac invention such as a high-risk percutaneous coronary intervention (PCI) or VF ablation. One convenient manner of placement of the distal portion of the pump 100A in the heart is by percutaneous access and delivery using a modified Seldinger technique or other methods familiar to cardiologists. These approaches enable the pump 100A to be used in emergency medicine, a catheter lab and in other medical settings. Modifications can also enable the pump 100A to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

The impeller assembly 116A can be expandable and collapsible. In the collapsed state, the distal end of the catheter pump 100A can be advanced to the heart, for example, through an artery. In the expanded state the impeller assembly 116A is able to pump blood at relatively high flow rates. In particular, the expandable cannula and impeller configuration allows for decoupling of the insertion size and flow rate, in other words, it allows for higher flow rates than would be possible through a lumen limited to the insertion size with all other things being equal. In FIGS. 1A and 1B, the impeller assembly 116A is illustrated in the expanded state. The collapsed state can be provided by advancing a distal end 170A of an elongate body 174A distally over the impeller assembly 116A to cause the impeller assembly 116A to collapse. This provides an outer profile throughout the catheter assembly and catheter pump 100A that is of small diameter during insertion, for example, to a catheter size of about 12.5 FR in various arrangements. In other embodiments, the impeller assembly 116A is not expandable.

The mechanical components rotatably supporting the impeller within the impeller assembly 116A permit relatively high rotational speeds while controlling heat and particle generation that can come with high speeds. The infusion system delivers a cooling and lubricating solution to the distal portion of the catheter pump 100A for these purposes. The space for delivery of this fluid is extremely limited. Some of the space is also used for return of the fluid supplied to the patient as waste fluid. Providing secure connection and reliable routing of the supplied fluid into and out of the catheter pump 100A is critical and challenging in view of the small profile of the catheter assembly.

When activated, the catheter pump 100A can effectively support, restore and/or increase the flow of blood out of the heart and through the patient's vascular system. In various embodiments disclosed herein, the pump 100A can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump 100A can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components can be combined with or substituted for those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following applications: U.S. Patent Publication No. US 2013/0303970, entitled "DISTAL BEARING SUPPORT," filed on Mar. 13, 2013; U.S. Patent Publication No. US 2014/0275725, entitled "FLUID HANDLING SYSTEM," filed on Mar. 11, 2014; U.S. Patent Publication No. US 2013/0303969, entitled "SHEATH SYSTEM FOR CATHETER PUMP," filed on Mar. 13, 2013; U.S. Patent Publication No. US 2013/0303830, entitled "IMPELLER FOR CATHETER PUMP," filed on Mar. 13, 2013; U.S. Patent Publication No. US 2014/0012065, entitled "CATHETER PUMP," filed on Mar. 13, 2013; and U.S. Patent Publication No. US 2014/0010686, entitled "MOTOR ASSEMBLY FOR CATHETER PUMP," filed on Mar. 13, 2013.

Moving from a distal end 1450 of the catheter assembly of the catheter pump 100A of FIG. 1B to a proximal end 1455, a priming apparatus 1400 can be disposed over the impeller assembly 116A. As explained above, the impeller assembly 116A can include an expandable cannula or housing and an impeller with one or more blades. As the impeller rotates, blood can be pumped proximally (or distally in some implementations) to function as a cardiac assist device.

In FIG. 1B the priming apparatus 1400 can be disposed over the impeller assembly 116A near the distal end portion 170A of the elongate body 174A. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. In some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400. A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter pump 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter pump 100A can be removed from the priming housing 1400 before a percutaneous heart procedure is performed, e.g., before the pump 100A is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients.

With continued reference to FIG. 1B, the elongate body 174A extends from the impeller assembly 116A in a proximal direction to an fluid supply device 195. The fluid supply device 195 is configured to allow for the supplied fluid to enter the catheter assembly 100A and/or for waste fluid to leave the catheter assembly 100A. A catheter body 120A (which also passes through the elongate body 174A) can extend proximally and couple to the motor assembly 1. As discussed in more detail herein, the motor assembly 1 can provide torque to a drive shaft that extends from the motor assembly 1 through the catheter body 120A to couple to an impeller shaft at or proximal to the impeller assembly 116A. The catheter body 120A can pass within the elongate body 174A such that the external elongate body 174A can axially translate relative to the internal catheter body 120A.

Further, as shown in FIG. 1B, a fluid supply line 6 can fluidly couple with the console 122 to supply saline or other fluid to the catheter pump 100A. The saline or other fluid can pass through an internal lumen of the internal catheter body 120A and can provide lubrication to the impeller assembly 116A and/or chemicals to the patient. The supplied fluid (e.g., saline or glucose solution) can be supplied to the patient by way of the catheter body 120 at any suitable flow rate. For example, in various embodiments, the fluid is supplied to the patient at a flow rate in a range of 15 mL/hr to 50 mL/hr, or more particularly, in a range of 20 mL/hr to 40 mL/hr, or more particularly, in a range of 25 mL/hr to 35 mL/hr. One or more electrical conduits 124 can provide electrical communication between the console 122 and the motor assembly 1. A controller within the console 122 can control the operation of the motor assembly 1 during use.

In addition, a waste line 7 can extend from the motor assembly 1 to a waste reservoir 126. Waste fluid from the catheter pump 100A can pass through the motor assembly 1 and out to the reservoir 126 by way of the waste line 7. In various embodiments, the waste fluid flows to the motor assembly 1 and the reservoir 126 at a flow rate which is lower than that at which the fluid is supplied to the patient. For example, some of the supplied fluid may flow out of the catheter body 120 and into the patient by way of one or more bearings. The waste fluid (e.g., a portion of the fluid which passes proximally back through the motor from the patient) may flow through the motor assembly 1 at any suitable flow rate, e.g., at a flow rate in a range of 5 mL/hr to 20 mL/hr, or more particularly, in a range of 10 mL/hr to 15 mL/hr.

Access can be provided to a proximal end of the catheter assembly of the catheter pump 100A prior to or during use. In one configuration, the catheter assembly 101 is delivered over a guidewire 235. The guidewire 235 may be conveniently extended through the entire length of the catheter assembly 101 of the catheter pump 100A and out of a proximal end 1455 of the catheter assembly 101. In various embodiments, the connection between the motor assembly 1 and the catheter assembly 101 is configured to be permanent, such that the catheter pump, the motor housing and the motor are disposable components. However, in other implementations, the coupling between the motor housing and the catheter assembly is disengageable, such that the motor and motor housing can be decoupled from the catheter assembly after use. In such embodiments, the catheter assembly distal of the motor can be disposable, and the motor and motor housing can be re-usable.

In addition, FIG. 1B illustrates the guidewire 235 extending from a proximal guidewire opening 237 in the motor assembly 1. Before inserting the catheter assembly 101 of the catheter pump 100A into a patient, a clinician may insert the guidewire 235 through the patient's vascular system to the heart to prepare a path for the impeller assembly 116A to the heart. In some embodiments, the catheter pump 100A can include a guidewire guide tube 20 (see FIG. 3) passing through a central internal lumen of the catheter pump 100A from the proximal guidewire opening 237. The guidewire guide tube 20 can be pre-installed in the catheter pump 100A to provide the clinician with a preformed pathway along which to insert the guidewire 235.

In one approach, the guidewire 235 is first placed through a needle into a peripheral blood vessel, and along the path between that blood vessel and the heart and into a heart chamber, e.g., into the left ventricle. Thereafter, a distal end opening of the catheter pump 100A and guidewire guide tube 20 can be advanced over the proximal end of the guidewire 235 to enable delivery to the catheter pump 100A. After the proximal end of the guidewire 235 is urged proximally within the catheter pump 100A and emerges from the guidewire opening 237 and/or guidewire guide 20, the catheter pump 100A can be advanced into the patient. In one method, the guidewire guide 20 is withdrawn proximally while holding the catheter pump 100A.

Alternatively, the clinician can thus insert the guidewire 235 through the proximal guidewire opening 237 and urge the guidewire 235 along the guidewire guide tube 20. The clinician can continue urging the guidewire 235 through the patient's vascular system until the distal end of the guidewire 235 is positioned in the desired position, e.g., in a chamber of the patient's heart, a major blood vessel or other source of blood. As shown in FIG. 1B, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart, blood vessel or other source of blood. The clinician can remove the guidewire 235 and the guidewire guide tube 20. The guidewire guide tube 20 can also be removed before or after the guidewire 235 is removed in some implementations.

After removing at least the guidewire 235, the clinician can activate the motor 1 to rotate the impeller and begin operation of the pump 100A.

Figure 2A:
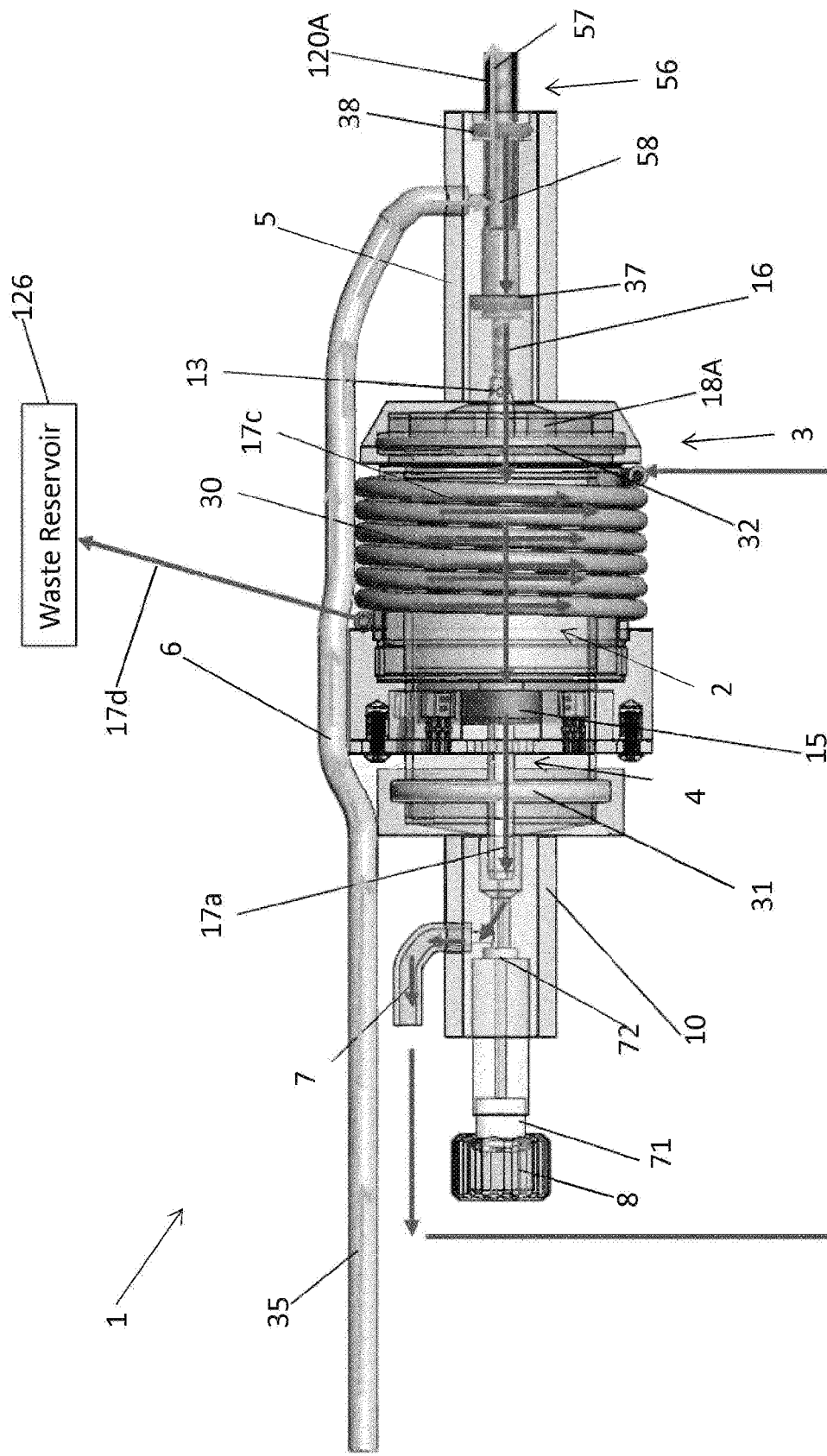
FIG. 2A is a side plan view of a motor assembly of the catheter pump system shown in FIG. 1B, according to one embodiment.
Figure 2C:
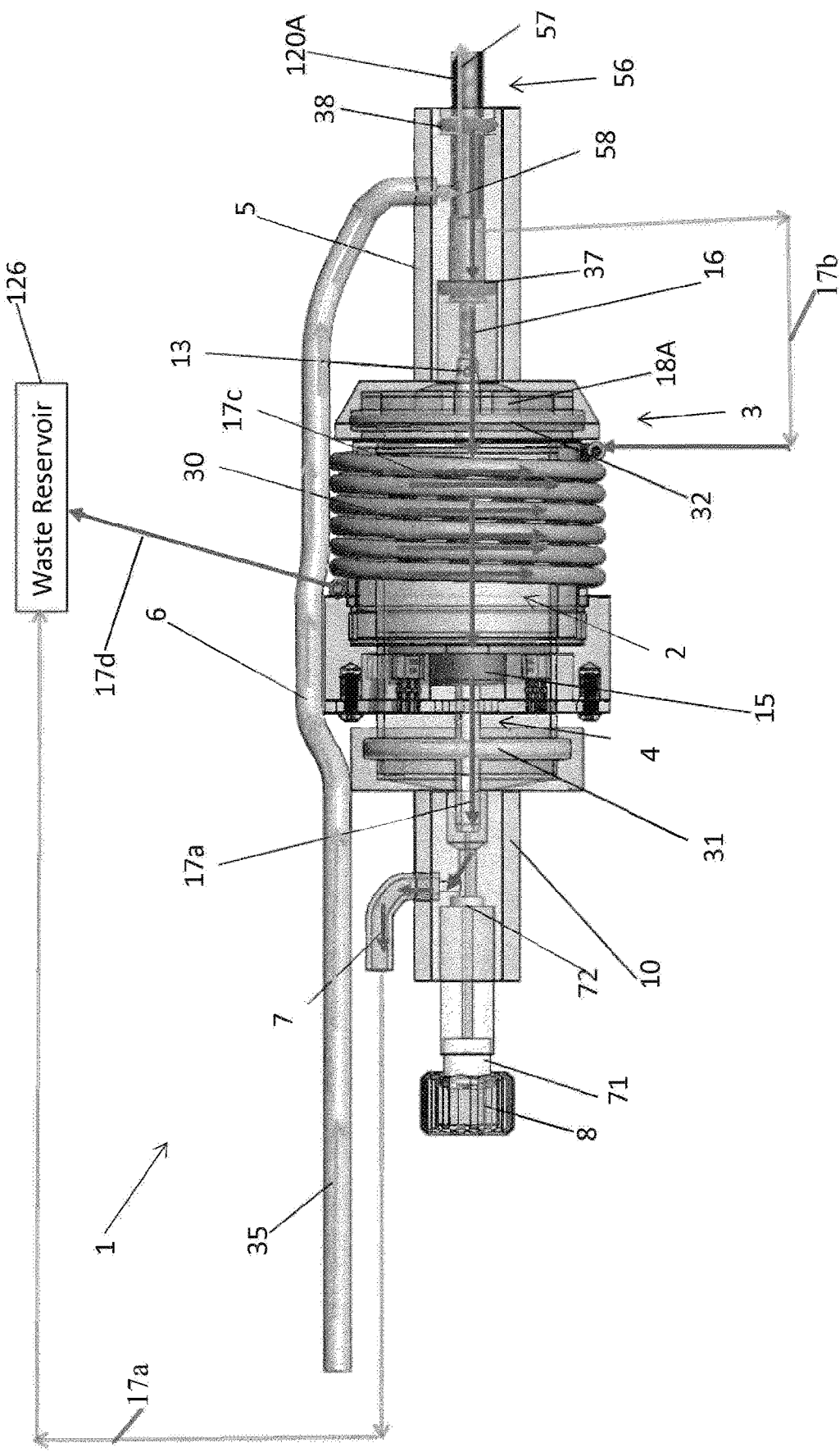
FIG. 2C is a side plan view of the motor assembly of the catheter pump system shown in FIG. 1B, according to yet another embodiment.

FIG. 2A is a side plan view of the motor assembly 1 shown in FIG. 1B, according to one embodiment. FIGS. 2B-2C are side plan views of the motor assembly 1 shown in FIG. 1B, according to other embodiments. FIG. 3 is a perspective exploded view of the motor assemblies 1 shown in FIGS. 2A-2C. The motor assembly 1 can include a stator assembly 2 and a rotor 15 disposed radially within the stator assembly 2. The motor assembly 1 also includes a flow diverter 3, which can be configured as a manifold for directing fluid through one or more passages in the catheter pump 100A. In some embodiments, the flow diverter 3 is at least partially disposed radially between the stator assembly 2 and the rotor 15. The flow diverter 3 can be fluidly sealed about the rotor 15 and a proximal portion 56 of the catheter body 120A. The seal prevents leakage and also can prevent the fluid from contacting the stator assembly 2. The flow diverter 3 can include a distal chamber 5 within which the proximal portion 56 of the catheter body 120A is disposed and a rotor chamber 4 within which the rotor 15 is disposed. The flow diverter 3 can also have a proximal chamber 10 in some embodiments. Where provided, the distal chamber 5, rotor chamber 4, and proximal chamber 10 can be in fluid communication within the flow diverter 3. In the illustrated embodiments, the distal chamber 5, the rotor chamber 4, and the proximal chamber 10 can be manufactured as three separate components and can be mechanically joined together to form the flow diverter 3. A first gasket (e.g., o-ring) 31 can be provided between the proximal chamber 10 and the rotor chamber 4 to fluidly seal the proximal chamber 10 and the rotor chamber 4. A second gasket 32 (e.g., o-ring) can be provided between the rotor chamber 4 and the distal chamber 5 to fluidly seal the connection between the rotor chamber 4 and the distal chamber 5. The use of the gaskets 31, 32 can simplify manufacturing and sealing compared with implementations in which the seals are formed by applying an adhesive about the periphery of the joined components. Thus, the first gasket 31 can prevent fluid from leaking outside the proximal chamber 10, e.g., at an interface between the proximal chamber 10 and the rotor chamber 4. The second gasket 32 can prevent fluid from leaking outside the distal chamber 5, e.g., at an interface between the distal chamber 5 and the rotor chamber 4.

One or more flanges 11A, 11B can mechanically couple the flow diverter 3 to an external housing (not shown). The flanges 11A, 11B are examples of mount structures that can be provided, which can include in various embodiments dampers to isolate the motor assembly 1 from external shock or vibration. In some embodiments, mount structures can include dampers configured to isolate an outer housing or the environment external to the motor assembly 1 from shock or vibration generated by the motor assembly 1. In addition, the guidewire guide tube 20 can extend proximally through the motor assembly 1 and can terminate at a tube end cap 8. As explained above, the guidewire 235 can be inserted within the guide tube 20 for guiding the catheter pump 100A to the heart.

The rotor 15 and stator assembly 2 can be configured as or be components of a frameless-style motor for driving the impeller assembly 116A at the distal end of the pump 100A. For example, the stator assembly 2 can comprise a stator and a plurality of conductive windings producing a controlled magnetic field. The rotor 15 can comprise a magnetic material, e.g., can include one or more permanent magnets. In some embodiments, the rotor 15 can comprise a multi-pole magnet, e.g., a four-pole or six-pole magnet. Providing changing electrical currents through the windings of the stator assembly 2 can create magnetic fields that interact with the rotor 15 to cause the rotor 15 to rotate. This is commonly referred to as commutation. The console 122 can provide electrical power (e.g., 24V) to the stator assembly 2 to drive the motor assembly 1. One or more leads can electrically communicate with the stator assembly 2, e.g., with one or more Hall sensors used to detect the speed and/or position of the motor. In other embodiments, other sensors (e.g., optical sensors) can be used to measure motor speed. The rotor 15 can be secured to an output shaft 13 (which can comprise a hollow shaft with a central lumen) such that rotation of the rotor 15 causes the output shaft 13 to rotate. In various embodiments, the motor assembly 1 can comprise a direct current (DC) brushless motor. In other embodiments, other types of motors can be used, such as AC motors, etc. As shown in FIG. 3, first and second journal bearings 18A, 18B can be provided about the output shaft 13 to radially and/or longitudinally center the output shaft 13 and thereby the rotor 15 relative to the stator assembly 2.

In various embodiments, it can be important to provide a heat removal system to limit buildup of heat in the motor assembly 1 during operation. For example, it can be important to maintain external surfaces of the motor assembly 1 at a temperature less than about 40° C. if the motor assembly 1 is positioned near the patient. For example, an external surface of an external housing 40 of the motor assembly 1 may be kept at or below this temperature. In some respects, regulatory guidelines can require that no part in contact with skin exceed 40° C. To that end, various strategies for heat management are employed by the inventions described herein. It should be appreciated that, as used herein, cooling refers to transferring away or dissipating heat, and in certain respects, cooling is used interchangeably with removing heat. Advantageously, some embodiments disclosed herein can utilize a heat removal system comprising one or more thermal layers which direct heat away from the heat-generating component (i.e., motor assembly 1) to reduce the temperature thereof. The one or more thermal layers may utilize waste fluid returning from the patient to remove heat in some embodiments. In other embodiments, the one or more thermal layers may be supplied with a coolant, such as a liquid or gaseous coolant, to cool the components of the motor assembly 1 and dissipate heat. In the embodiment illustrated in FIGS. 2A-3, for example, the thermal layer can comprise a heat exchanger 30, e.g., a coil which can be disposed about the stator assembly 2. For example, the coil of the heat exchanger 30 can be wrapped about a portion of the stator assembly 2 and can be disposed within a motor housing. In one embodiment, the heat exchanger 30 comprises a tubular body having a lumen. The tubular body and the lumen have a helical configuration where the inner diameter of the helix is larger than the outer diameter of the stator assembly. The tubular body and the lumen can have an outer diameter that is smaller than the inner periphery of the housing 40, discussed in more detail below. The coils of the helix can be tightly packed along a longitudinal axis of the helix, preferably close together but not touching. For example, adjacent centers of the lumen of the tubular body can be spaced apart by 110% of the outside diameter of the tubular body. As shown in FIGS. 2A-2C, the heat exchanger 30 can be axially positioned between a distal-most end of the stator assembly 2 and a proximal-most end of the stator assembly 2. Thus, the heat exchanger can comprise a volume to receive fluid for cooling the motor assembly. The volume of the heat exchanger to receive fluid can comprise an inner lumen of a coiled tube. In some embodiments, the volume of the heat exchanger to receive fluid can comprise a hollow portion of an annular cylinder, sleeve or jacket. The heat exchanger can be disposed about the stator in various embodiments disclosed herein.

Although the heat exchanger 30 is illustrated as a coiled lumen, e.g., as a helix, in FIGS. 2A-3, in other embodiments, the heat exchanger 30 can comprise an annular cylinder disposed about the stator assembly 2. For example, FIG. 3A is a schematic view of a heat exchanger 30A which may be used in any of the embodiments disclosed herein. The heat exchanger 30A can be shaped as an annular cylinder sized to be disposed about the stator assembly. Fluid can pass through the wall of the annular cylinder to dissipate heat from the motor assembly. In various embodiments, the heat exchanger 30 can comprise a jacket (e.g., a water jacket) or any other device which is at least partially disposed about the stator assembly 2. In various embodiments, the heat exchanger comprises one or more thermal layers such as those disclosed in U.S. application Ser. No. 13/953,547, filed Jul. 29, 2013, the entire contents of which application are incorporated by reference herein for all purposes.

The output shaft 13 (which is secured to the rotor 15) can be mechanically coupled with the proximal end portion of a drive shaft 16. The drive shaft 16 can extend distally through an internal lumen of the catheter body 120A. A distal end portion of the drive shaft 16 can mechanically connect with the impeller. Thus, rotation of the rotor 15 can cause the output shaft 13 to rotate, which, in turn, can cause the drive shaft 16 and the impeller to rotate. Further, a lumen can extend through the output shaft 13 and the rotor 15. In certain embodiments, the lumen of the rotor 15 is coupled with a lumen of the catheter body 120A such that the guidewire guide tube 20 can extend through the lumen within the rotor 15 and into the lumen of the catheter body 120A. In addition, the drive shaft 16 comprises a braided shaft having an internal lumen. The braided drive shaft 16 or cable can be permeable to liquid that can flow from outside the drive shaft 16 to within the internal lumen of the drive shaft 16 (and vice versa).

Further, as shown in FIGS. 2A-3, the tube end cap 8 can be welded or otherwise secured to a proximal end portion of the guide tube 20. The cap 8 can be removably engaged (e.g., screwed or removably locked) over a female receiver 71 that is secured in a proximal end of the proximal chamber 10. For example, the proximal end of the female receiver 71 can be disposed in a counterbore of the cap 8, while the guide tube 20 extends through the central opening of the cap 8. In a locked configuration, one or more tabs of the receiver 71 can be rotated such that the tab(s) slide under a corresponding tab in the counterbore of the cap 8. In an unlocked configuration, the tab(s) of the receiver 71 can be rotated relative to the tabs of the cap 8. FIG. 6 shows one embodiment of the cap 8 and of the female receiver 71 that can be coupled with the guide tube 20 (not shown). In the illustrated embodiment, the cap 8 can be fixed to the guide tube 20; in other embodiments, the receiver 71 can be fixed to the guide tube 20. Engaging the cap 8 to the receiver 71 can advantageously prevent the guide tube 20 from accidentally being removed from or slid within the catheter pump 100A, e.g., if the patient or clinician impacts the cap 8. To remove the guide tube 20 (e.g., after delivery of the impeller assembly 116A to the heart), the clinician can disengage the cap 8 from the receiver 71 and can pull the guide tube 20 from the catheter pump 100A, for example, by pulling proximally on the end cap 8. A resealable septum 72 can be provided at the proximal end of the flow diverter 3. When the guidewire guide 20 is removed from the pump 100A, the septum 72 will naturally reseal the pathway proximally from the motor assembly 1 such that fluid does not exit the assembly 1. An advantage of the exemplary assembly described herein is that the cap 8 is locked such that it will not be dislodged without rotating and unlocking cap 8 from receiver 71. With a conventional torquer assembly, the cap 8 can slide axially if it is inadvertently bumped by the patient or clinician. This potentially results in the guide tube 20 being pulled out from the distal-most end of the impeller assembly 116A, and because the guide tube cannot be re-inserted, the clinician either has to use the catheter pump 100A without a guide or get a new pump.

As explained above, it can be important to ensure that the motor assembly 1 is adequately cooled. Various components of the motor assembly 1 can generate heat. For example, moving parts within the motor assembly 1 (e.g., the rotating output shaft 13 and/or drive shaft 16) can generate heat by virtue of losses through friction, vibrations, and the like, which may increase the overall temperature of the motor assembly 1. Further, heat can be generated by the electrical current flowing through the stator assembly 2 and/or by induction heating caused by conductive components inside a rotating magnetic field. Furthermore, friction between the bearings 18 and the output shaft 13 and/or friction between the drive shaft 16 and the inner wall of catheter body 120A may also generate undesirable heat in the motor assembly. Inadequate cooling can result in temperature increases of the motor assembly 1, which can present patient discomfort, health risks, or performance losses. This can lead to undesirable usage limitations and engineering complexity, for example, by requiring mitigation for differential heat expansion of adjacent components of different materials. Accordingly, various embodiments disclosed herein can advantageously transfer away generated heat and cool the motor assembly 1 such that the operating temperature of the assembly 1 is sufficiently low to avoid such complexities of use or operation and/or other components of the system. For example, various heat transfer components and/or thermal layers can be used to move heat away from thermal generation sources and away from the patient. Various aspects of the illustrated device herein are designed to reduce the risk of hot spots, reduce the risk of heat spikes, and/or improve heat dissipation to the environment and away from the patient.

FIG. 2A illustrates an example of one embodiment for cooling the motor assembly 1. As shown in FIG. 2A, the supply line 6 can provide fluid 35 from a source (e.g., a fluid bag) to an outer lumen 57 of the catheter body 120A. The fluid 35 can travel distally toward the impeller assembly 116A to lubricate rotating components in the catheter assembly 101 and/or supply fluid to the patient. A first seal 37 (e.g., an o-ring) is an example of a fluid barrier that can be provided between the rotor housing 4 and the distal housing 5 to prevent backflow of the fluid 35 into the rotor housing 4. In this context, backflow is flow of fluid 35 proximally into the distal housing 5 rather than distally within the lumen 57. Such flow is to be prevented to ensure that the fluid 35 is initially exposed to moving parts in a distal portion of the catheter assembly 101 to lubricate and cool such distal components. A second seal 38 (e.g., an o-ring) is an example of another fluid barrier that can be provided near a distal opening of the distal chamber 5 to prevent fluid 35 from leaking outside the flow diverter 3 (e.g., out of the distal chamber 5).

A first portion 17*a* of fluid from the catheter pump 100A can flow proximally through an inner lumen 58 of the catheter body 120A. For example, after initially cooling distal components, some or all of the fluid 35 can flow within the drive shaft 16 and/or around the periphery of the drive shaft 16. After initially cooling distal components some or all of the fluid 35 can flow in a space disposed radially between the drive shaft 16 and the catheter body 120A. As shown in FIG. 2A, the cooling fluid 17*a* can flow into the rotor chamber 4 of the flow diverter 3. Some portions of the fluid 17*a* can pass proximally through the motor assembly 1 about a periphery of the rotor 15, e.g., in a gap between the rotor 15 and a wall of the flow diverter 3. In some embodiments, other portions of the fluid 17*a* can pass proximally through the motor assembly 1 through a lumen of the output shaft 13. The fluid portion 17*a* can pass from the rotor chamber 4 into the proximal chamber 10 of the flow diverter 3. The fluid 17*a* that passes proximally through the rotor chamber 4 (e.g., the portions that flow about the periphery of the rotor 15 and/or the portions that pass through the lumen of the output shaft 13) can advantageously convey heat away from the heat generating components. For example, portions of the cooling fluid 17*a* that pass about the periphery of the rotor 15 can direct heat radially outward from the rotor 15 and other components of the flow diverter 3, and radially inward from the stator assembly 2 and other components outside the flow diverter 3. Portions of the fluid 17*a* that pass through the lumen of the output shaft 13 can draw heat radially inward, e.g., radially inward from the rotor 15 and other components of the flow diverter 3. As the heat from the motor assembly 1 is conveyed away by way of the fluid to the waste reservoir, the temperature of the motor housing 1 can be reduced or maintained at a safe temperature for the patient and/or for the catheter pump system.

Thermal management of the motor assembly 1 can be improved by directing fluid through the heat exchanger 30. For example, in the embodiment of FIG. 2A, a second portion 17*b* of the fluid can pass through the line 7 and can be directed by a conduit to an inlet of the heat exchanger 30. A third portion 17*c* of the fluid can flow through the heat exchanger 30 circumferentially about the stator assembly 2.

A fourth portion 17*d* of the fluid can flow through an outlet of the heat exchanger 30 and into the waste reservoir 126. Heat generated by the motor assembly 1 can be directed radially outward from the stator assembly 2, the rotor chamber 4, and/or other heat generating components of the motor assembly 1, and can be conveyed away by the fluid 17*c* that flows through the heat exchanger 30 (e.g., within tubing or coils thereof). Thus, the embodiment of FIG. 2A can advantageously reduce the operating temperature of the motor assembly 1 to maintain the temperature of the motor assembly 1 at a suitable operational temperature for the medical staff, the patient and/or for the catheter pump system. Furthermore, although the heat exchanger 30 illustrated in FIG. 2A comprises coiled tubing, in other embodiments, the heat exchanger 30 can comprise an annular cylinder or other type of jacket which is disposed at least partially around the stator assembly 2. Like the illustrated embodiment, the use of a jacket or other type of heat exchanger can cool the motor assembly 1 by drawing heat radially outward from the components of the motor assembly 1. In the case where the motor assembly is resting near or against the patient, a jacket can also advantageously shield the patient from heat generated within the assembly to avoid injury and discomfort.

In the embodiment of FIG. 2A, the motor assembly 1 can comprise a fluid pathway for the proximally-flowing fluid 17*a*-17*d* to dissipate heat away from the motor assembly 1. For example, the fluid pathway can comprise a first portion through which the first fluid portion 17*a* flows (e.g., within the flow diverter 3). The fluid pathway can comprise a second portion comprising a conduit or tube which connects the first portion to the inlet of the heat exchanger 30 and through which the second fluid portion 17*b* flows. The fluid pathway can comprise a third portion comprising the heat exchanger 30 and through which the third fluid portion 17*c* flows. The fluid pathway can comprise a fourth portion comprising a conduit or tubing connected to the waste reservoir 126 and through which the fourth fluid portion 17*d* flows.

FIG. 2B illustrates an example of another embodiment for cooling the motor assembly 1. Unless otherwise noted, components numbered similar to those in FIG. 2A represent the same or similar components and functionalities. For example, a first fluid portion 35*a* (e.g., saline) can flow along the supply line 6 and can be directed distally through an outer lumen 57 of the catheter body 120A. The first portion 35*a* can comprise saline, glucose, or other biocompatible fluids in various arrangements. A first portion 17*a* of the proximally-flowing fluid can return proximally through an inner lumen 58 of the catheter body 120A. The fluid 17*a* can flow within the drive shaft 16 and/or around the periphery of the drive shaft 16. As shown in FIG. 2B, the fluid 17*a* can flow into the rotor chamber 4 of the flow diverter 3. Some portions of the fluid 17*a* can pass proximally through the motor assembly 1 about a periphery of the rotor 15, e.g., in a gap between the rotor 15 and a wall of the flow diverter 3. Other portions of the fluid 17*a* can pass proximally through the motor assembly 1 through the lumen of the output shaft 13. The fluid 17*a* can pass from the rotor chamber 4 into the proximal chamber 10 of the flow diverter 3. The fluid 17*a* that passes proximally through the rotor chamber 4 (e.g., the portions that flow about the periphery of the rotor 15 and/or the portions that pass through the lumen of the output shaft 13) can advantageously convey heat away from the heat generating components. For example, portions of the fluid 17*a* that pass about the periphery of the rotor 15 can direct heat radially outward from the rotor 15 and other components of the flow diverter 3, and radially inward from the stator assembly 2 and other components outside the flow diverter 3. Portions of the fluid 17a that pass through the lumen of the output shaft 13 can draw heat radially inward, e.g., radially inward from the rotor 15 and other components of the flow diverter 3. As the heat from the motor assembly 1 is conveyed away by way of the fluid to the waste reservoir, the temperature of the motor housing 1 can be reduced or maintained at a safe temperature for the patient and/or for the catheter pump system.

Unlike the embodiment of FIG. 2A, in the embodiment of FIG. 2B, a second portion 17b of the proximally-flowing cooling fluid can be directed to the waste reservoir 126 by way of the waste line 7. Thus, in FIG. 2B, the fluid 17b is not redirected into the heat exchanger 30. Instead, a second fluid portion 35b is directed into an inlet of the heat exchanger 30. A third fluid portion 35c can flow through the heat exchanger 30 circumferentially about the stator assembly 2. A fourth fluid portion 35d can flow through an outlet of the heat exchanger 30 and into the waste reservoir 126. The coolant that flows through the fluid portions 35a, 35b, 35c, and 35d can be saline or another coolant that need not be biocompatible. Heat generated by the motor assembly 1 can be directed radially outward from the stator assembly 2, the rotor chamber 4, and/or other heat generating components of the motor assembly 1, and can be conveyed away by the third fluid portion 35c that flows within the tubing of the heat exchanger 30. Thus, the embodiment of FIG. 2B can advantageously reduce the operating temperature of the motor assembly 1 such that temperature of the motor assembly is maintained at a suitable operational temperature for the medical staff, the patient and/or for the catheter pump system. A gap between the stator assembly and the external motor housing 40 (e.g., the outer shell or housing surrounding the motor assembly) comprises air, which is a good, natural insulator. Thus, the heat from the stator assembly 2 is naturally transferred to the waste line rather than dissipating out the sides of the housing 40 of the motor assembly 1.

Although the fluid 35 is described as comprising saline in some embodiments, it should be appreciated that other fluids (such as refrigerants, e.g., R134) can be used within the heat exchanger 30. For example, in other embodiments, a first portion 39a of a cooling fluid 39 other than the supply fluid (e.g., other than saline) can be supplied to an inlet of the heat exchanger 30. A second portion 39b of the cooling fluid can pass through the heat exchanger 30 to draw heat away from the motor assembly. A third portion 39c of the cooling fluid can be conveyed through an outlet of the heat exchanger 30 and into the waste reservoir 126. The cooling fluid 39 can comprise any suitable type of fluid, e.g., any suitable cooling liquid or gas. For example, in some embodiments, the cooling fluid 39 can comprise a refrigerant such as R134A can be used. In other embodiments, water or another liquid may be used as the cooling fluid 39. In still other embodiments, the cooling fluid 39 can comprise a gas, such as air, nitrogen, etc. For example, in some embodiments, the cooling fluid 39 can comprise air supplied by pressurized air systems that are frequently available in hospitals and other clinical settings. The use of such conventional pressurized air systems can advantageously reduce the number of external supply reservoirs provided with the catheter pump system, which can reduce costs and simplify packaging. Furthermore, a chiller or other cooling apparatus can be provided upstream of the heat exchanger 30 to cool the supplied fluid 35 and/or cooling fluid 39 prior to the fluid 35 and/or cooling fluid 39 entering the heat exchanger 30.

Cooling the fluid 35 and/or cooling fluid 39 can advantageously improve the thermal management of the motor assembly 1. Advantageously, using a cooling fluid 39 which is different from the fluid 35 supplied to the patient may reduce the temperature to a greater degree than using the fluid 35 alone. For example, the cooling fluid 39 may have superior heat transfer qualities relative to the fluid 35.

In the embodiment of FIG. 2B, the motor assembly 1 can comprise a first fluid pathway for the fluid 35a supplied to the patient, a second fluid pathway for the proximally-flowing fluid 17a-17b, and a third fluid pathway for the fluid supplied to the heat exchanger (e.g., the fluid 35b-d or 39a-c). For example, the first fluid pathway can comprise a conduit in fluid communication with an inner lumen of the catheter body which travels distally tot he treatment location. The second fluid pathway can comprise a first portion through which the first fluid portion 17a flows (e.g., within the flow diverter 3) and a second portion through which the fluid portion 17b flows to the waste reservoir 126. The third fluid pathway can comprise a first portion comprising a tube or conduit which conveys the fluid 35b, 39a to the inlet of the heat exchanger 30 and a second portion comprising the heat exchanger 30 and through which the fluid portion 35c, 39b flows. The third fluid pathway can comprise a third portion comprising a conduit or tubing connected to the waste reservoir 126 and through which the fluid portion 35d, 39c flows.

FIG. 2C illustrates yet an example of another embodiment for cooling the motor assembly 1. Unless otherwise noted, components numbered similar to those in FIG. 2A represent the same or similar components and functionalities. For example, as with the embodiment of FIG. 2A, a first portion 17a of the proximally-flowing fluid can pass within the motor assembly 1, for example, about a periphery of the rotor 15, e.g., in a gap between the rotor 15 and a wall of the flow diverter 3. In some embodiments, other portions of the fluid 17a can pass proximally through the motor assembly 1 through a lumen of the output shaft 13. In the embodiment of FIG. 2A, the fluid is directed to the heat exchanger 30 after passing through the flow diverter 3. Unlike the embodiment of FIG. 2A, in the embodiment of FIG. 2C, a second portion 17b of the proximally-flowing fluid can be shunted from the flow diverter 3 before passing within and/or around the rotor 15. For example, an outlet line can direct the second portion 17b of the fluid out of the flow diverter 3 and to the inlet of the heat exchanger 30. A third portion 17c of the fluid can pass through the heat exchanger 30 to draw heat radially outward from the stator assembly 2 and other components of the motor assembly 1. A fourth portion 17d of the fluid can be conveyed to the waste reservoir 126. Furthermore, unlike the embodiment of FIG. 2A, in the embodiment of FIG. 2C, the first portion 17a of the fluid can be directed to the waste reservoir 126 after passing through the flow diverter 3.

In the embodiment of FIG. 2C, the motor assembly 1 can comprise a fluid pathway for the proximally-flowing fluid 17a-17d to dissipate heat away from the motor assembly 1. For example, the fluid pathway can comprise a first portion through which the fluid portion 17a flows (e.g., within the flow diverter 3). The fluid pathway can comprise a second portion which splits off from the first portion of the fluid pathway and comprises a conduit or tube which connects to the inlet of the heat exchanger 30 and through which the second fluid portion 17b flows. The fluid pathway can comprise a third portion comprising the heat exchanger 30 and through which the third fluid portion 17c flows. The fluid pathway can comprise a fourth portion comprising a conduit or tubing connected to the waste reservoir 126 and through which the fourth fluid portion 17*d* flows.

Still other thermal management techniques may be suitable in combination with the embodiments disclosed herein. For example, U.S. Patent Publication Nos. 2014/0031606 and 2011/0295345, which are incorporated by reference herein in their entirety and for all purposes, describe structures and materials which may be incorporated in place of or in addition to the devices described above to manage heat effectively, as will be understood by one of skill from the description herein. Furthermore, as explained herein, the heat exchanger 30 can comprise any suitable shape or configuration. For example, the heat exchanger 30 can comprise a jacket (such as an annular cylinder or sleeve) disposed about the stator assembly 2 in some embodiments. In some embodiments, the systems disclosed in FIGS. 1A-4 can ensure that the temperature of the exterior surface of the motor assembly 1 is not more than about 40° C. In some embodiments, the systems disclosed in FIGS. 1A-4 can ensure that the temperature of the exterior surface of the motor assembly 1 is in a range of 15° C. to 42° C., or more particularly in a range of 20° C. to 42° C., in a range of 20° C. to 40° C., in a range of 20° C. to 35° C., or in a range of 20° C. to 30° C., without requiring the use of external cooling fins exposed outside the motor housing.

Operation of the motor assembly 1 may also generate undesirable vibrations. For example, high magnitude vibrations can be inconvenient for the patient or clinician, and/or can damage components of the motor assembly 1. One way that vibrations are reduced and controlled in the disclosed embodiments is by providing the journal bearings 18A, 18B (FIG. 3) on opposite axial sides of the rotor 15 to help maintain the rotor 15 in radial alignment with the rotor chamber 4 and in axial alignment with the stator assembly 2. Improving radial alignment of the rotor 15 and output shaft 13 relative to the rotor chamber 4 can reduce or eliminate eccentricity during rotation, which can reduce vibrations. Improving axial alignment relative to the stator assembly 2 can advantageously improve the efficiency of the motor assembly 1 by ensuring that the windings of the stator assembly 2 remain precisely aligned with the rotor 15. In various embodiments, the journal bearings 18A, 18B can be rotationally decoupled with the output shaft 13 such that the output shaft 13 can rotate relative to the bearings 18A, 18B. In some embodiments, the journal bearings 18A, 18B can be fixed inside the rotor chamber 4. Moreover, one or more passages can be provided in the bearings 18A, 18B so that cooling fluid can pass axially through the bearings 18A, 18B. For example, the bearings 18A, 18B can form radially-extending arms with one or more gaps disposed between the arms. Such gaps can be enclosed peripherally by a housing enclosing the stator assembly 2. In other embodiments, one or more openings can be provided through the bearings 18A, 18B to define the passages. Furthermore, by using a single rotating permanent magnet as opposed to multiple rotating magnets, vibrations may be reduced.

Figure 4:
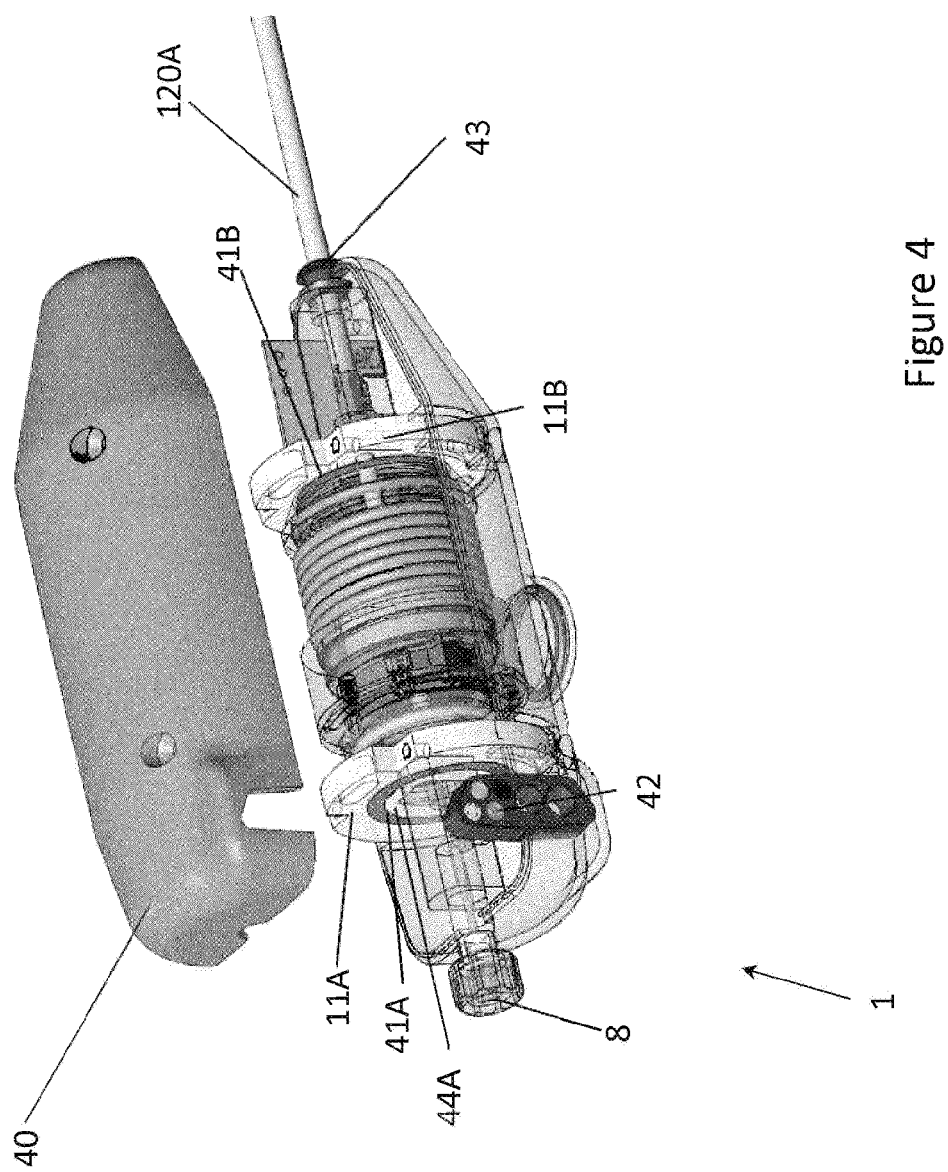
FIG. 4 is a schematic perspective view of the motor assembly with various vibration-reducing components.

FIG. 4 is a schematic perspective view of the motor assembly 1 with various other vibration-reducing components. For example, the flanges 11A, 11B can be disposed about the flow diverter 3 and can mechanically couple with an interior surface of a motor housing 40.

In various embodiments, dampening elements are used to limit or eliminate transmission of vibration and noise from the rotating portions of the motor assembly 1 to the rest of the motor assembly (e.g. housing 40). In various embodiments, the rotation elements are connected to the stationary elements only through damping elements. A damping element 41A, 41B can be disposed radially within the flanges 11A, 11B. An inner flange portion 44A, 44B can be disposed radially inward of the damping element 41A, 41B. Suitable materials and structures for the damping elements include, but are not limited to, rubber, elastomers, polymers, springs, and the like. In the illustrated embodiments, the damping element 41A, 41B is formed of rubber, a thermoplastic elastomer (e.g., polyurethane), or other damping materials understood by one of skill in the art. In various embodiments, the damping elements comprise an anti-vibration mount formed of a relatively rigid element and a compression element. The inner flange portion 44A, 44B can be secured about the outer surface of the flow diverter 3. In the illustrated embodiments, the inner flange portions 44A, 44B and the flanges 11A, 11B can be stiffer than the damping elements 41A, 41B. For example, in some embodiments, the inner flange portions 44A, 44B and the flanges 11A, 11B can comprise a plastic material and the damping element 41A, 41B can comprise rubber.

Vibrations may be caused by the rotating components of the motor assembly 1, e.g., by rotation of the rotor 15, the output shaft 13, the drive shaft 16, etc. The vibrations can be transmitted outwardly through the inner flange portions 44A, 44B to the damping elements 41A, 41B. The damping elements 41A, 41B can damp the amplitude of the vibrations such that minimal or no vibrations are transmitted through the flanges 11A, 11B to the housing 40. Thus, the use of the flanges 11A, 11B, the damping elements 41A, 41B, and the inner flange portions 44A, 44B can advantageously reduce the transmission of vibrations to the housing 40 and the patient. In various embodiments, the damping elements 41A, 41B can comprise one or more windows therethrough that provide for the routing of fluid and/or electrical lines through the motor assembly 1. Routing fluid and/or electrical lines through these windows can isolate the fluid and/or electrical lines from strain that may be induced by rotating or moving components.

In addition, vibrations can also be caused by rotation of the drive shaft 16, for example, when the drive shaft 16 hits the catheter body 120A. To reduce vibrations caused by rotation of the drive shaft 15, a fitting 43 can be disposed in an opening of the motor housing 40 about the catheter body 120A. The fitting 43 can comprise any suitable fitting that damps vibrations (e.g., rubber). For example, the fitting 43 can comprise a grommet disposed about the catheter body 120A. Vibrations generated by the rotating drive shaft 16 can be transmitted outwardly through the catheter body 120A and can be damped by the fitting 43. The fitting 43 can thereby attenuate and/or eliminate vibrations from being transmitted to the motor housing 40.

A strain relief feature 42 can also be provided on the exterior of the motor housing 40. The strain relief feature 42 can comprise a plurality of holes through which wires can be routed to the motor assembly 1. The strain relief feature 42 can help to route the wires and can prevent the patient or clinician from accidentally pulling on the wires that are connected to the motor assembly 1.

In addition, the embodiments of the motor assembly 1 disclosed herein are advantageously of smaller dimensions and smaller weight as compared with motor assemblies that use two rotating magnets, e.g., a drive magnet and a follower magnet. In one example, a breadboard built according to the description above was found to reduce the overall length of the motor assembly 1 by about 20% and the overall weight by about 40% by comparison to an equivalent assembly with rotor magnet and follower magnet.

Figure 5A:
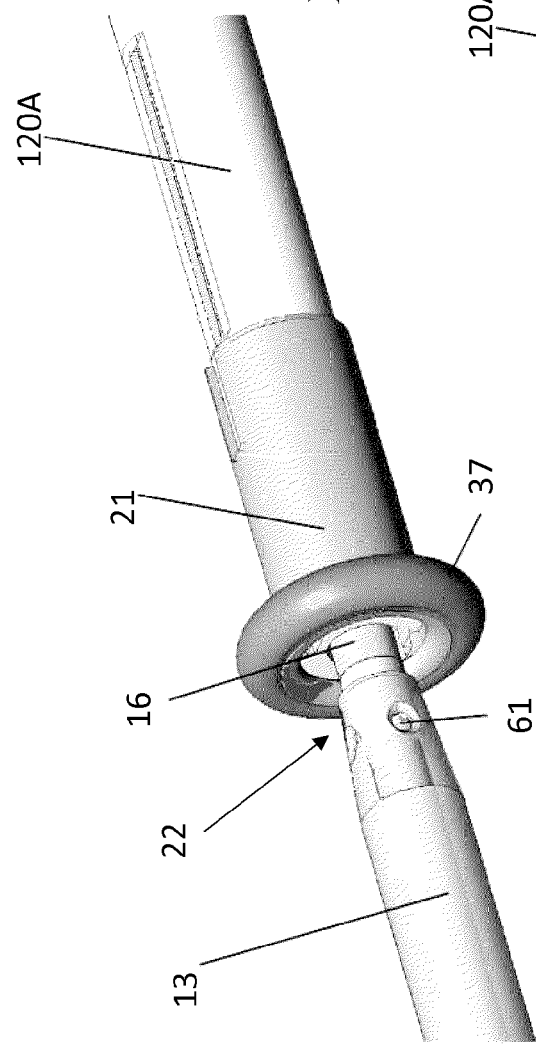
FIG. 5A is a schematic perspective view of an interface between an output shaft of the motor assembly and a drive shaft of the catheter pump.
Figure 5B:
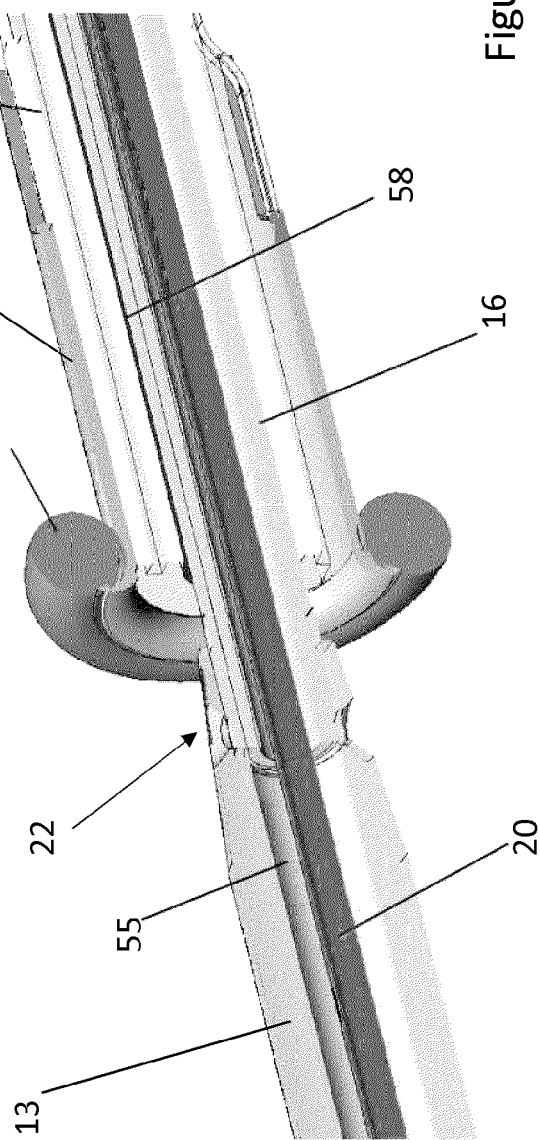
FIG. 5B is a cross-sectional perspective view, taken through the longitudinal axis of the catheter, showing more details of the interface shown in FIG. 5A.

FIGS. 5A and 5B show one embodiment of an interface 22 between the output shaft 13 and the drive shaft 16. The interface 22 can comprise a connection between a distal portion of the output shaft 13 and a proximal portion of the drive shaft 16. The distal portion of the output shaft 13 can comprise a radially-inward taper and one or more holes 61 formed through the output shaft 13. The proximal portion of the drive shaft 16 can be inserted within the lumen 55 of the output shaft 13 such that the lumen 55 and the inner lumen 58 of the catheter body 120A form a continuous passage. This passage can be used to advance the guidewire guide tube 20, sensors, and other instruments, or to provide fluid communication for cooling fluid or medications. Cooling fluid can flow proximally from the inner lumen 58 of the catheter body 120 and portions of the fluid can pass outwardly about the periphery of the rotor 15. Other portions of the fluid can pass through the lumen 55 of the output shaft 13. A sleeve 21 can be disposed about the proximal portion of the catheter body 120A, and the seal 37 can be provided about the sleeve 21 to seal the distal chamber 5 from the rotor chamber 4.

In the illustrated embodiments, the output shaft 13 can be permanently coupled with, e.g., laser welded to the drive shaft 16. For example, a welding machine can access the interface 22 by way of the holes 61 formed in the output shaft 13 to weld the output shaft 13 to the drive shaft 16. In other embodiments, the output shaft 13 can be secured to the drive shaft 16 in other ways, e.g., by friction or interference fit, by adhesives, by mechanical fasteners, etc.

Although the embodiments disclosed herein illustrate examples of heat transfer devices (such as the heat exchanger 30), it should be appreciated that other types of heat transfer devices may be suitable. For example, a thermal layer can be disposed within the housing and configured to transfer heat away from the stator and/or the rotor. At least a portion of the thermal layer can be disposed between the rotor and the stator assembly. In some embodiments, the thermal layer and heat transfer system may be employed without requiring external fins which are exposed to the outside environs. In other embodiments, heat fins or other conductive elements can assist in transferring heat away from the stator and/or rotor and to the environment. For example, in some embodiments, internal heat fins or other conductive elements may be disposed within the motor assembly 1 about the stator assembly 2, but may not be exposed to the outside environs. In some embodiments, a fan can be disposed inside the motor housing to assist in dissipating heat. In some embodiments, the motor housing can comprise holes or vents to cause air to flow over the internal heat fins. In some embodiments, at least a portion of the thermal layer is disposed within the rotor, e.g., a lumen disposed within the rotor. In some embodiments, the thermal layer comprises a thermally conductive material. In some embodiments, the thermal layer comprises an inside layer of high thermal conductivity (for absorbing heat spikes) and an outer layer of low thermal conductivity (for dissipating heat into the environment slowly). The thermal layer can also comprise a fluid pipe. In some embodiments, the thermal layer comprises a fluid chamber, the rotor configured to be disposed in fluid in the fluid chamber. In some embodiments, the thermal layer comprises a heat exchanger with a plurality of coils, the coils disposed about a portion of the stator assembly 2 (or other parts of the motor assembly 1). In some embodiments, as explained above, the thermal layer can comprise a heat exchanger comprising a jacket or sleeve (e.g., an annular cylinder) disposed about a portion of the stator assembly 2 and/or other parts of the motor assembly 1.

Although the embodiments disclosed herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump system comprising:
   an impeller;
   a catheter body having a supply lumen therethrough, and through which a first fluid is supplied to a distal portion of the catheter body;
   a drive shaft disposed inside the catheter body and coupled with the impeller at a distal portion of the drive shaft; and
   a motor assembly comprising:
   a rotor mechanically coupled with a proximal portion of the drive shaft; and
   a stator assembly disposed about the rotor and configured to cause the rotor to rotate; and
   a heat exchanger coupled with the motor assembly to remove heat therefrom, the heat exchanger comprising a volume to receive a second fluid, wherein the heat exchanger is disposed about a portion of the stator assembly, and wherein the volume is in fluid isolation from the supply lumen of the catheter body.

2. The catheter pump system of claim 1, wherein the first fluid is a biocompatible coolant fluid.

3. The catheter pump system of claim 1, wherein the second fluid is a non-biocompatible coolant fluid.

4. The catheter pump system of claim 3, wherein the second fluid comprises a refrigerant.

5. The catheter pump system of claim 3, wherein the second fluid comprises a compressed gas.

6. The catheter pump system of claim 1, wherein the heat exchanger further comprises tubing defining a lumen therethrough that further defines the volume that receives the second fluid, the lumen extending from an inlet to an outlet, the inlet in fluid communication with a supply reservoir, and the outlet in fluid communication with a waste reservoir.

7. The catheter pump system of claim 6 further comprising a chiller coupled in fluid communication between the supply reservoir and the inlet of the heat exchanger, the chiller configured to cool the second fluid prior to its flowing into the inlet of the heat exchanger.

8. The catheter pump system of claim 1, wherein the motor assembly further comprises a chamber in fluid communication with the supply lumen of the catheter body and in fluid isolation from the heat exchanger volume, wherein the rotor is disposed in the chamber.

9. The catheter pump system of claim 8, wherein the first fluid flows proximally from the supply lumen into the chamber and about a periphery of the rotor.

10. The catheter pump system of claim 8, wherein the first fluid flows proximally from the supply lumen into the chamber and through a lumen of an output shaft of the rotor.

11. The catheter pump system of claim 8 further comprising a waste reservoir in fluid communication with an outlet of the chamber of the motor assembly, and wherein the first fluid flows proximally from the supply lumen into the chamber and through the outlet to the waste reservoir.

12. A method of cooling a motor of a catheter pump system, the method comprising:
  directing a distal flow of a first fluid through a supply lumen of a catheter body of the catheter pump system, the catheter body having a drive shaft disposed therein and coupled to an impeller at a distal portion of the drive shaft;
  directing a proximal flow of the first fluid through a chamber of a motor assembly of the catheter pump system, the chamber having a rotor of the motor assembly disposed therein; and
  directing a coolant flow through a lumen of a heat exchanger coupled about a portion of a stator assembly of the motor assembly, the lumen in fluid isolation from the supply lumen.

13. The method of claim 12, wherein directing the proximal flow further comprises directing at least a portion of the proximal flow about a periphery of the rotor in a gap defined between the rotor and a wall of the motor assembly.

14. The method of claim 12, wherein directing the proximal flow further comprises directing at least a portion of the proximal flow through a lumen defined in an output shaft of the rotor.

15. The method of claim 12, wherein directing the distal flow further comprises enabling a return flow proximally from the distal portion of the catheter body through an inner lumen of the catheter body.

16. The method of claim 15, wherein enabling the return flow further comprises coupling a waste reservoir in fluid communication with the inner lumen of the catheter body.

17. The method of claim 12, wherein directing the proximal flow further comprises coupling a waste reservoir in fluid communication with the chamber.

18. The method of claim 12, wherein directing the coolant flow further comprises coupling a non-biocompatible supply reservoir in fluid communication with an inlet of the lumen defined through the heat exchanger, and coupling a waste reservoir in fluid communication with an outlet of the lumen.

19. The method of claim 18, wherein directing the coolant flow further comprises directing a refrigerant through the lumen defined through the heat exchanger.

20. The method of claim 18, wherein directing the coolant flow further comprises directing the coolant flow through a chiller coupled in fluid communication between the non-biocompatible supply reservoir and the inlet of the lumen.

* * * * *